(12) United States Patent
Kaufman et al.

(10) Patent No.: US 9,460,262 B2
(45) Date of Patent: Oct. 4, 2016

(54) DETECTING AND RESPONDING TO SENTINEL EVENTS

(75) Inventors: Andrew Kaufman, Fayetteville, NY (US); James Knoll, Syracuse, NY (US); Bruce Way, Three Mile Bay, NY (US)

(73) Assignee: The Research Foundation of State University of New York, Albany, NY (US)

( * ) Notice: Subject to any disclaimer, the term of this patent is extended or adjusted under 35 U.S.C. 154(b) by 199 days.

(21) Appl. No.: 14/127,035

(22) PCT Filed: Jun. 15, 2012

(86) PCT No.: PCT/US2012/042735
§ 371 (c)(1),
(2), (4) Date: Oct. 8, 2014

(87) PCT Pub. No.: WO2012/174420
PCT Pub. Date: Dec. 20, 2012

(65) Prior Publication Data
US 2015/0077245 A1 Mar. 19, 2015

Related U.S. Application Data

(60) Provisional application No. 61/576,704, filed on Dec. 16, 2011, provisional application No. 61/498,388, filed on Jun. 17, 2011.

(51) Int. Cl.
| G08B 1/08 | (2006.01) |
|---|---|
| G06F 19/00 | (2011.01) |
| A61B 5/0205 | (2006.01) |
| A61B 5/024 | (2006.01) |

(Continued)

(52) U.S. Cl.
CPC .......... *G06F 19/3418* (2013.01); *A61B 5/024* (2013.01); *A61B 5/0205* (2013.01); *A61B 5/14551* (2013.01); *A61B 5/165* (2013.01); *A61B 5/746* (2013.01); *G08B 21/02* (2013.01)

(58) Field of Classification Search
CPC  A61B 5/0205; A61B 5/024; A61B 5/14551; A61B 5/165; A61B 5/746; G08B 21/02; G06F 19/3418
USPC ....... 340/539.1–539.18, 573.1; 600/300, 301
See application file for complete search history.

(56) References Cited

U.S. PATENT DOCUMENTS

| 7,500,950 B2 * | 3/2009 | Al-Ali .................. A61B 5/0002 600/300 |
|---|---|---|
| 7,558,622 B2 | 7/2009 | Tran |

(Continued)

FOREIGN PATENT DOCUMENTS

| WO | WO-2007073455 A1 | 6/2007 |
|---|---|---|
| WO | WO-2010105053 A2 | 9/2010 |

OTHER PUBLICATIONS

ISA/US, International Search Report and Written Opinion for Corresponding International Application No. PCT/US12/42735 mailed Jan. 23, 2013 (13 pgs).

*Primary Examiner* — Eric M Blount
(74) *Attorney, Agent, or Firm* — Harris Beach PLLC

(57) ABSTRACT

The present invention is directed to systems, devices, and methods of monitoring at-risk individuals for the occurrence of sentinel events in a custodial care setting. In particular, the present invention is directed to monitoring for events such as suicide, and allowing monitoring personnel to actively respond to the event and prevent its success from occurring.

32 Claims, 5 Drawing Sheets

(51) Int. Cl.
*A61B 5/1455* (2006.01)
*A61B 5/16* (2006.01)
*A61B 5/00* (2006.01)
*G08B 21/02* (2006.01)

(56) References Cited

U.S. PATENT DOCUMENTS

| | | |
|---|---|---|
| 8,140,143 B2 | 3/2012 | Picard et al. |
| 2003/0212579 A1* | 11/2003 | Brown ............... A61B 5/411 705/2 |
| 2004/0030531 A1* | 2/2004 | Miller ............... A61B 5/0002 702/182 |
| 2004/0260154 A1* | 12/2004 | Sidelnik ............ A61B 5/0205 600/300 |
| 2010/0056935 A1* | 3/2010 | McKinley ......... A61B 5/4076 600/504 |
| 2010/0280336 A1* | 11/2010 | Giftakis ............ A61B 5/0476 600/301 |
| 2011/0112860 A1 | 5/2011 | Kehr |
| 2011/0118555 A1* | 5/2011 | Dhumne ............... A61B 5/16 600/300 |
| 2011/0245633 A1 | 10/2011 | Goldberg et al. |
| 2011/0260870 A1 | 10/2011 | Bailey |
| 2011/0306846 A1* | 12/2011 | Osorio ............... A61B 5/4094 600/301 |
| 2013/0046153 A1* | 2/2013 | Hyde ............... A61B 5/4833 600/302 |

* cited by examiner

_____

DETECTING AND RESPONDING TO SENTINEL EVENTS

CROSS-REFERENCE TO RELATED APPLICATIONS

This application is a national stage application under 35 U.S.C. §371 of PCT Application No. PCT/US2012/042735, filed Jun. 15, 2012, which claims priority to and the benefit of U.S. Provisional Application Ser. No. 61/498,388, filed Jun. 17, 2011 and U.S. Provisional Application Ser. No. 61/576,704, filed Dec. 16, 2011, which are incorporated herein by reference in their entirety.

FIELD OF THE INVENTION

This disclosure relates generally to the monitoring and prevention of various sentinel events, such as death. More specifically, this disclosure relates to monitoring one of several physiological characteristics for changes which would indicate likelihood of impending death.

BACKGROUND OF THE INVENTION

The rate of suicide among individuals in custodial care settings, such as psychiatrically hospitalized patients and inmates in jails and prisons, is high. The rate of suicide in psychiatric facilities has reportedly ranged from 100-400 per 100,000 admissions across the U.S., China, New Zealand, Australia, Austria, and the United Kingdom. In the US alone this amounts to about 1,500 suicide deaths per year and, since there are estimated to be about 12.5 suicide attempts per completed suicide, about 19,000 suicide attempts. The suicide rate among jail inmates is reportedly 5 to 9 times higher and, among prison inmates, 1.5 to 2 times higher than that of the general population. Given the high rate of suicides, individuals in custodial care settings have been deemed "at-risk" individuals, in need of monitoring and control. Typically, such at-risk individuals are monitored by staff members of the institution on a regular basis, such as in 15-minute intervals. Other times, the at-risk individual is monitored by video surveillance, where the person monitoring is able to visually check the monitored patient on a regular basis. Again, however, such monitoring often is not continuous, and relies upon monitoring on a regular basis, such as every ten to fifteen minutes. This regular monitoring and individual surveillance not only takes time and effort, but also adds an increasingly high financial cost to the institution. Even despite this regular observation there is still a high likelihood of attempted and successful suicides. The majority of the completed suicides still occur between the times that the individual is monitored, without the knowledge of the person monitoring the individual until the act has already been committed. In one study, 9% of these suicides occurred under continuous individual on-on-one supervision or monitoring by a trained staff member. The most common method of suicide employed by this population is hanging/strangulation, which has an estimated fatality rate of greater than 70%. A study of 696 jail suicide deaths from 2005-2006 revealed that 93% occurred by hanging. A study of 76 prison suicides in New York from 1993-2001 showed 86.1% occurred by hanging. In a study in England and Wales from 1996-2000, 175 of 234 (75%) of suicides on psychiatric wards were caused by hanging, with one third of these occurring in toilet or bathroom setting. A U.S. study of 76 inpatient suicides showed that 61% occurred by hanging, the most frequent method. Suffocation, such as by placing one's head in a plastic bag or blocking one's airway with an object or objects, is also employed by these populations.

SUMMARY OF THE INVENTION

In accordance with one aspect of the disclosure, a method of detecting and responding to a sentinel event by an at-risk individual is provided, wherein the at-risk individual is maintained in a custodial care setting by at least one monitoring personnel. The method includes a step of securing a monitoring device above the neckline of the at-risk individual. The monitoring device is adapted with a sensor to collect data on at least one physiological characteristic selected from the group consisting of pulse amplitude, heart rate, and blood oxygen saturation of the at-risk individual. The method further includes the steps of establishing a first criterion for each physiological characteristic that, if met, will cause an alert to be initiated, and monitoring the at least one physiological characteristic of said at-risk individual. A processor analyzes the sensor data collected by the monitoring device on each at least one physiological characteristic to determine if said first criterion for initiating an alert has been met for said at least one physiological characteristic and, if so, initiates an alert to the at least one monitoring personnel that the first criterion has been met for the at least one physiological characteristic.

In another aspect of the invention, a system for detecting a sentinel event by an at-risk individual is provided. The system includes a monitoring device adapted to be worn above the neck of the at-risk individual, the monitoring device including a sensor adapted to monitor at least one physiological characteristic of the at-risk individual. The system further includes a first transmitter in communication with the sensor. The first transmitter is adapted to send data relating to the at least one physiological characteristic. The system further includes a base station including a first receiver and a second transmitter. The first receiver is adapted to receive the physiological characteristic data from the monitoring device, and the second transmitter is adapted to transmit an alert message. The system further includes an alert device including a second receiver to receive the alert message, and a signal generator adapted to generate an alert in the form of an audible, visual or tactile alarm. The system further includes a computer-readable medium and a processor coupled to the computer-readable medium. The processor is adapted to execute program instructions to analyze data from the sensor of the at least one monitoring device, determine if a sentinel event has begun or is occurring and, if so, initiate an alert to the alert device.

BRIEF DESCRIPTION OF THE DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

DETAILED DESCRIPTION OF THE INVENTION

Figure 1:
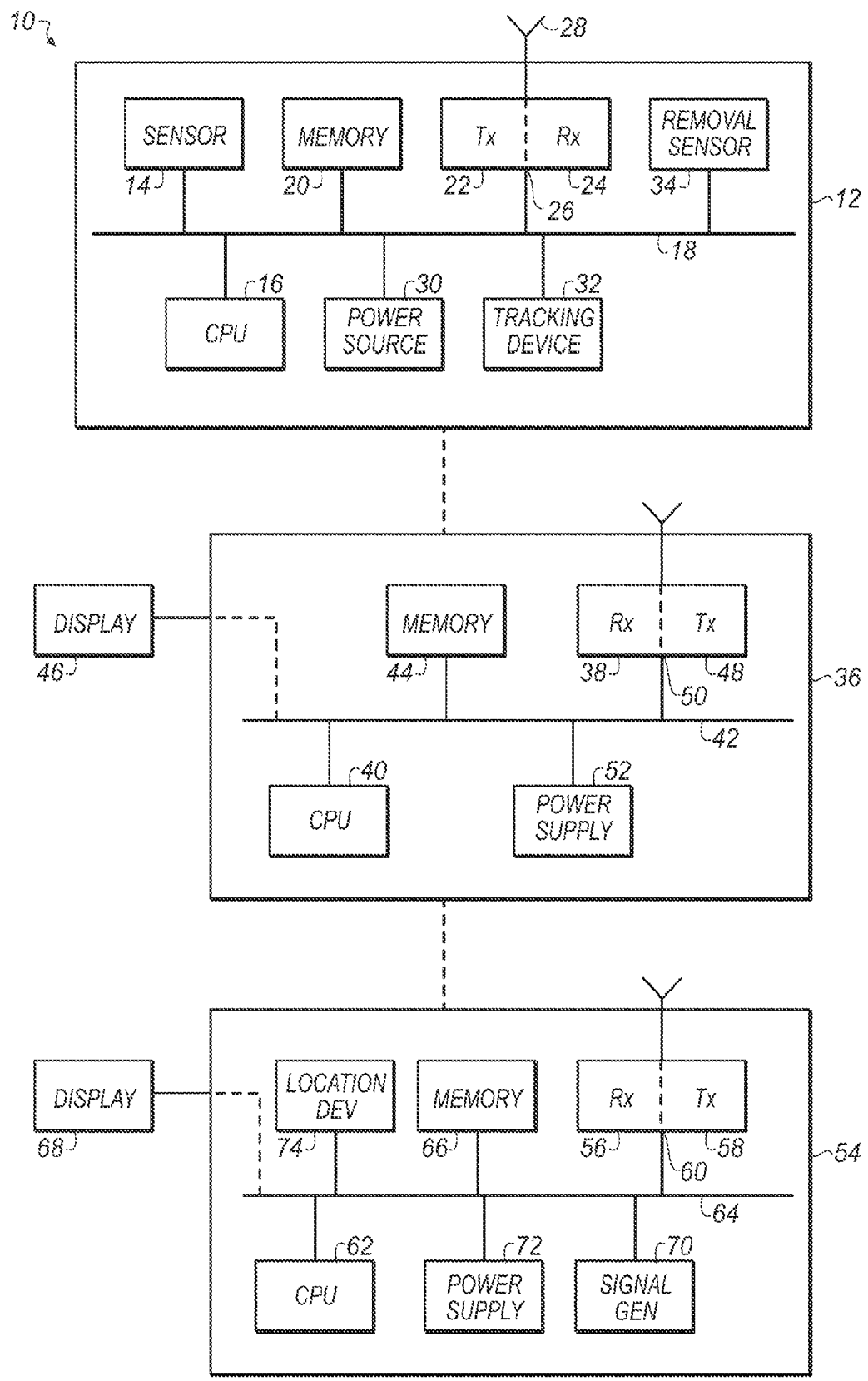
FIG. 1 depicts a block diagram of a system for detecting sentinel events, according to one embodiment of the invention.

As used herein, the terms "at-risk individual" and "individual at an elevated risk of suicide" may be used interchangeably, and are intended to refer to a person who is likely to suffer from death or other physical bodily harm, such as through a sentinel event including for example, suicide, drug or medication use, including overdose or toxicity, panic attack, drug/alcohol withdrawal, stroke, cardiac arrhythmia, or heart attack. In one embodiment, an "at-risk individual" is one who is more likely than an average person to attempt suicide, and may include individuals who are kept in a custodial care setting, as defined below. In another embodiment, an "at-risk individual" may include a person who is more likely than an average person to suffer a heart attack or other heart problem due to that individual's likelihood to engage in drugs, alcohol, or other medication, which may cause a cardiac, circulatory or respiratory problem due to its use, misuse, overdose or withdrawal. Further, in another embodiment, an "at-risk individual" may include a person who is more likely than an average person to suffer from severe panic attacks, thereby running the risk of endangering that individual's body, including intense psychological distress that may be compared to suffering a heart attack. At-risk individuals may be those individuals who are likely to suffer from heart attack or stroke, such as elderly individuals.

As used herein, the term "custodial care setting" refers to an institution where individuals are kept under care and/or watch. Examples of custodial care settings include hospitals, psychiatric institutions, jails and prisons, juvenile detention centers, assisted living facilities, group homes, rehabilitation facilities (substance abuse and medical/physical), nursing home facilities, and the like. A custodial care setting is not necessarily limited to an institution in which an individual is kept against his or her will, and may include voluntary admission hospitals and rehabilitation centers.

As used herein, a "physiological characteristic" is a characteristic of an individual's body that can be monitored, and may include, among other characteristics, a pulse, heart rate, blood oxygen saturation, breathing rate, and perspiration levels. Other characteristics that may be monitored include blood pressure, tissue perfusion (amount of blood flow to specific tissue), urine output, EKG tracing, electroencephalography (EEG), body weight, exhaled $CO_2$ levels, and central venous pressure.

Embodiments of the present invention are directed to an apparatus for and a method of monitoring at least one at-risk individual for sentinel events. Further embodiments of the invention are directed to an apparatus for and method of preventing sentinel events resulting in serious injury or death. In one embodiment, a sentinel event may result in death, while in other embodiments a sentinel event may result in severe bodily harm, such as brain damage. Sentinel events may include suicide and attempted suicide, which may result in harm, including death. However, such an act may be classified as a sentinel event even if the suicide is unsuccessful, because the individual can cause severe or irreversible bodily damage, such as brain damage. In some embodiments, the act may be classified as sentinel even if no body damage occurs. A sentinel event may also include death or severe body damage, or no body damage through non-suicide related activities, such as ingestion of or withdrawal of drugs, alcohol or other medication. Further, a sentinel event may include death or severe bodily damage, or no body damage through suffering an involuntary action, such as a panic attack or a seizure.

The invention seeks to monitor for the likelihood of sentinel events occurring, and alerting at least one monitoring personnel of the sentinel event as early as possible. Monitoring personnel include any staff members, employees or agents of the custodial care setting, and may include, for example, doctors, physician assistants, nurse practitioners, nurses, police officers, patient care technicians, mental health technicians, nursing assistants, health aides, correctional officers, counselors, therapists, psychologists, social workers, or other clinicians. By alerting at least one monitoring personnel as early as possible, it has been discovered that the risk of harm from a sentinel event may be greatly reduced, if not eliminated. For example, the invention provides a method of determining whether an at-risk individual is attempting suicide, alerting at least one monitoring personnel when a suicide attempt is identified and preferably with the location of the suicide attempt, and the monitoring personnel responding to the alert by checking on the at-risk individual. The monitoring personnel may be able to check on the at-risk individual with enough time to prevent the sentinel event. As will be explained in more detail below, the sentinel event is not limited to suicide attempts, and includes other events that may occur to at-risk individuals. Embodiments of the present invention are useful for monitoring the presence of any of several sentinel events through a plurality of monitoring tools.

In one embodiment, the present invention provides an apparatus and method for monitoring and detecting suicide attempts by an at-risk individual, particularly an at-risk individual kept in a custodial care setting. The most common means of suicide by an at-risk individual is hanging or strangulation by securing an article (ligature) around the individual's neck, and allowing it to tighten around the neck due to the force of gravity on the mass of the body. Often, an at-risk individual attempts suicide by hanging in an isolated area, such as a bathroom or bedroom in the custodial care setting, where in-person monitoring is not always performed. When an individual attempts to hang one's self, a number of physical changes occur very quickly. Typically, the article used compresses the internal and external carotid arteries in the individual's neck, immediately blocking blood flow, thereby reducing the pulse amplitude above the neck, such as at the ears, temples, scalp, forehead, earlobe, or other pulse locations. The change in pulse amplitude, or termination of detectable pulse, should occur almost immediately. In some embodiments, the termination of a detectable pulse occurs within about 5 to about 10 seconds, and in most instances, occurs within less than 5 seconds. Therefore, in one embodiment a device triggers an alarm when the pulse amplitude drops to a level such that the device can no longer detect a pulse, as will be explained below. In some instances, the individual's breathing is compromised, reducing the oxygen levels in the individual's blood. At a blood oxygen saturation of 89% or below, vital organs do not receive sufficient oxygen to function, and thus a blood oxygen saturation of 90% or less indicates potential hazard.

Another means of attempted suicide is via asphyxiation, where the individual deliberately takes steps to block his ability to breathe. Such method may occur, for example, by the individual forcing objects into his mouth and throat, or by covering his mouth and nose with an airtight material. Typically, this method compromises the individual's breathing, and thus reduces the oxygen levels in the individual's blood. At a blood oxygen saturation of 89% or below, the vital organs do not receive sufficient oxygen to function properly. The reduction of oxygen saturation occurs within a few seconds to about three minutes, depending upon the level of occlusion and the baseline health of the individual.

As noted above, sentinel events are not limited to suicide attempts, and may include events that are not deliberately undertaken by the at-risk individual. For example, certain at-risk individuals may be likely to suffer from panic attacks, alcohol or drug withdrawal complications, or other physical and emotional states that raise the blood pressure and heart rate to dangerous levels. When an individual suffers from a panic attack, for example, the pulse rate of the individual increases by about 15-20 more beats per minute, or more. It is known that an increase in pulse above 120 (or alternatively, below 60) is significant, and should be addressed. The increase in pulse for a panic attack occurs within about 5 to about 20 seconds after the attack begins.

Another sentinel event may include an at-risk individual taking an overdose of narcotics, drugs or medication, which may have a dangerous effect on that individual's heart or brain. For example, taking a stimulant may rapidly increase the individual's heart rate and pulse, indicating that the narcotic has been taken. Taking an opiate, such as heroin or morphine, for example, may cause the individual's brain's breathing regulation center to be inhibited, thus reducing the inhalation of oxygen and resulting in a decrease in blood oxygen saturation. As explained above, a decrease in blood oxygen levels below 89% may cause vital organs to fail. This increase in heart rate and/or pulse, or drop in blood oxygen saturation may reach dangerous levels.

With the understanding of the changes in the physiological characteristics when any of the above sentinel events occurs, the embodiments of the present invention are able to monitor at-risk individuals, alert personnel, and thus reduce the likelihood of a successful or harmful event from occurring. For ease of explanation, reference will be made to one particular event, suicide, but it is to be understood that the following method is applicable to any event that changes one or more physiological characteristics.

Referring now to FIG. 1, in one embodiment, there is provided a system 10 for monitoring patients to detect sentinel events and alert staff so that a timely response can be achieved. The system 10 includes a patient-worn monitoring device 12 incorporating a sensor 14 capable of monitoring at least one physiological characteristic. The physiological characteristic may include heart rate, pulse rate, pulse amplitude, presence of a pulse, or oxygenation level of the blood, for example. In one embodiment, the sensor 14 is a pulse sensor for measuring or detecting the presence or absence of a wearer's pulse and an oximeter for measuring the level of oxygen saturation of the wearer's blood. In another embodiment, the sensor 14 a pulse oximeter for measuring both pulse and oxygen levels in the blood of the individual. In one example, the sensor 14 is a pulse oximeter such as that manufactured by Nonin Medical, Inc. (Plymouth, Minn.) under the trade name WristOx2. The pulse oximeter contains two parts, each with individual components. The sensor 14, which interfaces directly with the individual to be monitored, contains a light emitting diode and a light detector. The light is typically in the infrared spectrum. The oximeter contains integrated circuitry that processes the signal from the light detector and a power source. The invention may be coupled with a Life Systems, Inc. monitoring system for wireless receiving of signal and data storage and retrieval. Other oximeters and monitoring systems may be used if desired, such as the E1 Ear Sensor from Masimo and the in-ear sensor for pulse oximetry designed by CiS Forschungsinstitut für Mikrosensorik and Photovoltaik GmbH.

The monitoring device 12 may further include a processor 16 coupled to a system bus 18. The bus 18 can connect other system components, such as the sensor 14, to the processor 16. The processor 16 can execute computer program instructions or program code for carrying out operational functions of the monitoring device 12, such as processing and saving data from the sensor 14, managing transmissions, implementing power saving protocols, determining the monitoring device's location, and determining when a sentinel event has occurred, such as by comparing actual sensor data to baseline data for the wearer. The processor 16 may be a microprocessor, an application-specific integrated circuit (ASIC), or other programmable data processing apparatus to produce a machine, such that the program instructions, which execute via the processor, create means for implementing the functions/acts specified in the flowcharts, block diagrams, and/or detailed description disclosed herein.

The monitoring device 12 may further include one or more computer-readable medium(s) 20 (e.g., memory) coupled to the system bus 18. The computer-readable medium 20 may be a computer-readable signal medium or a computer-readable storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include a random access memory (RAM), a read-only memory (ROM), an erasable programmable read-only memory (EPROM or Flash memory), or any suitable combination of the foregoing.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

The computer-readable medium 20 may have embodied thereon data related to the particular individual who will be wearing the monitoring device 12. For example, the computer-readable medium 20 may include data such as the at-risk individual's name, age, identifying physical characteristics, as well as information related to the individual's psychiatric needs and evaluation. For example, in the case of a patient in a mental care institution, particulars as to the patient's psychiatric needs and information related to his evaluation may be highly beneficial in stopping the event from occurring or preventing the individual from continuing the attempt.

The computer-readable medium 20 may have embodied thereon information related to baseline levels and ongoing monitoring of one or more physiological characteristics specific to the individual to whom the device is assigned. As will be explained in more detail below, each individual has a unique baseline level for such characteristics as heart rate, pulse rate and blood oxygen levels. The ability to store this baseline can improve the functionality of the device.

The monitoring device 12 may further include a transmitter 22 to communicate data to and from a base station, the function of which will be discussed in more detail below. In one embodiment of the present invention, the transmitter 22 includes a variety of components that perform various tasks or functions. For example, the components may include a radio frequency (RF) signal modulator, an RF signal amplifier, and an RF signal tuner. The RF signal modulator includes any suitable structure for modulating data onto an outgoing RF signal for transmission. The RF signal amplifier includes any suitable structure for amplifying RF signals. The RF signal tuner includes any suitable structure for tuning the transmitter 22 to a specified RF frequency or frequencies.

In another embodiment of the invention, the monitoring device 12 further includes a receiver 24, as will be discussed in detail below. The receiver 24 may include an RF signal demodulator comprising any suitable structure for demodulating data in an incoming RF signal. The transmitter 22 and the receiver 24 could be integrated as a transceiver 26, for example. The transmission and/or reception of RF signals could occur using an antenna 28, which represents any suitable structure capable of transmitting and receiving RF or other wireless signals.

The monitoring device 12 may further include a portable power source 30 to provide electrical energy for the various components of the monitoring device, such as the sensor 14, the processor 16, or the first transmitter 22. The power source 30 may comprise a battery (disposable or rechargeable), an inertial generator, solar cells, a chemical energy source, a betavoltaic device, an induction energy capture device, an antennae for harvesting electromagnetic or acoustical energy (such as RF waves), or other power storage, capture or generating device. In one embodiment, the power source 30 and its housing are adapted for quick removal such that a fully charged battery may take its place without disrupting the function of the device. A seal (not shown) between the battery compartment and the other components may comprise an O-ring or other waterproof technology to be consistent with the overall waterproof design of the monitoring device 12.

The monitoring device 12 may include a tracking device 32 for determining the location of the monitoring device 12. The tracking device 32 or the other component of the system may be capable of determining the precise location of the monitoring device 12 with respect to the institution in which the device is being used. For example, the tracking device 32 may be capable of determining the particular floor, wing, or room in the building in which the device is operating at any time. The ability of the tracking device 32 to determine and communicate its location aids in the invention by providing enabling one or more monitoring personnel to be informed of the exact location of the at-risk individual at the time a sentinel event is identified, allowing for a more prompt response time. As noted above, with a prompt response time, the likelihood of preventing the sentinel event from resulting in death or serious bodily injury is increased.

The tracking device 32 can be any device or system used for determining the location of an object. In one example, the tracking device 32 utilizes satellites in a Global Positioning System to determine the location of the monitoring device 12 from externally broadcast signals. In another example, the tracking device 32 is an inertial system that uses dead reckoning to determine the location of the monitoring device 12. In other examples, the tracking device 32 utilizes radio frequency triangulation, or emits a beacon that is captured by the base station to locate the monitoring device 12. The beacon may include a data signal transmitted by the first transmitter 22. Inertial sensors, if incorporated into the monitoring device can also detect sudden, perhaps unexpected, rapid or unusual, changes in a patient's position as well as a lack of movement, and the monitoring device can then send the information from the inertial sensor to the base station or staff. Inertial sensors could also detect falls by the wearer, especially those of sufficient height to cause serious injury or death. The monitoring system can be set to trigger an alert if a fall of a certain magnitude or at a certain location is detected, or if the at-risk individual is determined to be climbing above the floor or ground. The various methods of locating and tracking the motion of the monitoring device and the person wearing it can be used separately or in any combination.

Since the monitoring device 12 is used to monitor for one or more physiological characteristics of the at-risk individual, the device may be secured to the body of the at-risk individual. In one example, the monitoring device 12 is secured to the individual at a location at which the device can monitor at least one physiological characteristic. In one example, the monitoring device 12 is secured to the individual at a location above the neckline Securing the monitoring device 12 above the neckline can provide significant benefits over other locations on the body, especially in preventing a sentinel event due to hanging. Hanging causes constriction of the neck as a result of the weight of the body forcing the neck against a ligature. The ligature constricts the arteries, thus reducing or completely obstructing blood flow in the arterial and venous system. Sometimes, the airway (trachea) is also blocked. The arteries constricted in anatomical location of typical ligature include the common carotid, internal and external carotid. Once blood flow is reduced/blocked, the arterial supply distal to the blockage is compromised. This results in hypoxemia (reduced oxygen) in the tissues of the head which leads ultimately to brain death. The blood supply to the scalp, ear and other surface structures of the head mirrors the status of the blood supply to the brain, itself.

Securing the monitoring device 12 above the neckline allows the device to detect changes in blood flow above the neck, for example, upon compression of the carotid arteries (two on each side). The presence/absence of pulse, pulse amplitude, and blood oxygen saturation measured at various anatomical sites above the ligature point on the neck reflect the blood supply to the brain. Suitable locations for the monitoring device 12 include in the ear, the forehead, the scalp, the temple, behind the ear, and on the neck itself. Any superficial sites on the head which are accessible to pulse oximetry sensors would be appropriate for this application, in that they share the following attributes: blood flow near the skin surface supplied by carotid arteries; the sensor can be applied on opposite sides of tissue or the sensor can be applied on single side of tissue (reflectance monitor); and a sensor can be affixed to the anatomical site. These include, but are not limited to: earlobe, ear auricle, auditory canal, forehead, temple, jaw, chin, cheek, scalp, post-auricular area (behind ear), occipital area (back of neck/head), nose, nostrils. In one example, the device is small enough to be non-obtrusive to the user, but still capable of detecting for changes in one or more characteristic.

In one embodiment, the monitoring device 12 is capable of attaching to the ear of the at-risk individual, which is an unobtrusive location. In some embodiments, the device may be clipped or strapped to the ear lobe of the individual, or inserted into the ear canal or secured mechanically in the concha of the pinna (outer ear). In still other embodiments, the monitoring device 12 may be secured to the user's body via an adhesive. In one embodiment, the monitoring device 12 can be worn for an extended period of time, such as days, weeks, months or years, without risk of being dislodged. To allow for continuous monitoring, the monitoring device 12 should be kept on the body of the user continuously, during waking and sleeping times. Further, the monitoring device 12 may be waterproof, so as to allow use in wet environments, such as showers. Since this monitoring device 12 can be similar in size to a hearing aid, and will be worn for long periods of time like a hearing aid, any of the various hearing aid designs used over the years, and the means by which hearing aid components are secured to the ear, can be modified for use for the present device. Designs for Bluetooth headsets which are worn on the ear can also be adapted for use with the monitoring device.

Sensors 14 may be secured to anatomical sites by a variety of methods. The desirable attributes of a mechanism or means of attachment allow that the sensor 14 securely remains on person, is comfortable to wear, and maintains constant contact with skin/anatomical surface to provide continuous reliable signal, and that the attachment mechanism or means or the sensor do not damage structural integrity of skin/surface, cause significant irritation to skin/surface, or directly contact internal anatomical structures. Among the mechanisms that can be utilized are: adhesive material; elastic material; belts, necklaces, or bands (such as headband, wristband, and ankle band) with buckles, clasps, ties, snaps, Velcro, buttons, etc.; magnets; springs; mechanical devices which complement anatomical structure, such as an ear cuff; pressure fit devices; and mechanisms that insert into anatomical cavities, such as the ear canal.

The monitoring device 12 may further include a removal sensor 34 to detect removal of the monitoring device. The removal sensor 34 can comprise any device capable of indicating when the patient-worn monitoring device is removed by the patient, such as a pair of electrodes measuring skin resistance, a thermocouple measuring skin temperature, and a spring-loaded mechanical switch that is in one position when the device is worn and one when it is removed (e.g., it springs open when the device is pulled off). In one embodiment, the pulse oximeter sensor 14 can be used as a removal detection sensor.

The components of the patient-worn monitoring device 12 can be separate, interconnected devices, or some or all of them can be integrated into a single integrated circuit or into a single package. For example, the sensor 14, processor 16, memory 20, and transmitter 22 can be part of a single integrated circuit. An exemplary in-ear sensor suitable for pulse-oximetry is manufactured by designed by CiS Forschungsinstitut für Mikrosensorik and Photovoltaik GmbH. The device uses a highly integrated design to achieve an extremely compact device incorporating at least some of the above components.

The patient-worn monitoring device is small enough to be non-obtrusive to the user and desirably adapted to be secured to the body of the at-risk individual at a location at which the device can monitor at least one physiological characteristic, most desirably, a location above the neckline. Suitable locations for the device include in the ear, the forehead, the scalp, the temple, behind the ear, and on the neck itself.

The system 10 further includes a base station 36 for receiving data from the patient-worn monitors and transmitting alerts to the alert devices. The monitoring device 12 communicates with a receiver 38 in the base station 36 that communicates with a processor 40 connected to a system bus 42. The processor 40 can execute computer program instructions or program code for carrying out operational functions of the base station 36, such as processing and saving data from the monitoring device 12, managing transmissions, determining the monitoring device's location, and determining when a sentinel event has occurred, such as by comparing actual sensor data to baseline data for the wearer. The processor 40 may be a microprocessor, an application-specific integrated circuit (ASIC), or other programmable data processing apparatus to produce a machine, such that the program instructions, which execute via the processor, create means for implementing the functions/acts specified in the flowcharts, block diagrams, and/or detailed description disclosed herein.

The processor 40 may communicate with a computer-readable medium 44 (e.g., memory) via the system bus 42. The computer-readable medium or memory 44 may be a computer-readable signal medium or a computer-readable storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include a random access memory (RAM), a read-only memory (ROM), an erasable programmable read-only memory (EPROM or Flash memory), or any suitable combination of the foregoing.

More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, radio frequency (RF), etc.

Program code embodied on a computer-readable medium may be transmitted using any appropriate medium, including but not limited to wireless, wireline, optical fiber cable, RF, etc., or any suitable combination of the foregoing.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The memory 44 can store data from monitored individuals. In one embodiment, the patient-worn monitoring device 12 transmits raw data, and the processor 40 on the base station 36 can run programs to analyze the raw data to determine when a sentinel event has begun or is occurring. The processor 40 in the base station 36 may receive the raw data from the patient-worn monitor 12 and process that data with information stored in the memory 44, such as baseline patient data, to determine whether a sentinel event has occurred. Thus, the processor 40 can be programmed to include in its calculations the individual's identity, clinical data, and baseline physiologic parameters.

In some embodiments, software running on the processor 40 will also provide a graphical user interface (GUI) for personnel to adjust customized settings. The GUI may appear on a display 46 connected to an output of the base station 36.

The base station 36 may also run programs that allow it to determine the location of the patient-worn monitoring device 12 using the signal received from it. For example, the processor 40 may calculate the differences in the strength or timing of the same signal received by different receivers in the system.

The base station 36 can transmit alerts via a transmitter 48 and may run programs that aid in coordinating the response to an alert. The receiver 38 and the transmitter 48 may be integrated to form a transceiver 50. If an alert device (discussed below) has both a receiver and a transmitter, the base station 36 and the alert device may be programmed to interact to assist staff in coordinating a response to an alert. When a sentinel event is determined to have occurred, the base station 36 can transmit to the alert devices an alert signal, and if it is available, the location at which the event occurred. The base station 36 may also periodically transmit a signal to the alert devices that everything is working and that there are no problems. In one embodiment there are multiple base stations. In another embodiment the base station is portable.

The base station 36 further includes a power supply 52, which for the base station could be the electrical grid (e.g., 120-volt alternating current) or any appropriate power source. The base station 36 may include a backup power source (not shown) such as uninterruptable power supply (UPS), battery, or generator to keep the base station operating in case of a power outage.

In the illustrated embodiment there is provided at least one base station receiver 38 capable of receiving communications from the monitoring device 12. In other embodiments, there may be a plurality of receivers, each capable of receiving information from the monitoring device 12. For example, there may be one central receiver, which is monitored by monitoring personnel who may respond to any communications or alerts provided by the monitoring device 12. Optionally, the receivers may be wireless and portable, so that a plurality of monitoring personnel are able to carry a receiver with them. The receiver(s) should further be capable of receiving communications from a plurality of monitoring devices.

The receiver(s) should be capable of providing an alert, such as an audible alarm, visual alarm, or vibrational/tactile alarm. Further, it is desirable that the receiver include a means of communicating information to the monitoring personnel regarding the particular monitoring device communicating with the receiver. For example, the receiver 38 may include a visual communication means, such as a display, map, or other visual aspect. The receiver 38 may include an audible communication means, such as a speaker. For example, if monitoring device 12 communicates with a receiver 38, the receiver may communicate details stored in the memory 20 of device 12, including, for example, the individual's name, the location of the individual, and the reason for the communication (i.e., that the blood oxygen level in the individual has decreased). It is particularly desirable that the communication between the monitoring device and the receiver(s) be substantially instantaneous, i.e., within less than 5 seconds, within less than 3 seconds, or most desirably, within 1 second.

The monitoring device 12 should be capable of communicating with at least one receiver 38 upon certain predetermined criteria being met. In the absence of the predetermined criteria being met, the monitoring device 38 will not communicate with the receiver. Alternatively, the device 12 may provide a constant or repeated signal to the at least one receiver 38, which provides the monitoring personnel with the assurance that the monitoring device is working. An alert may sound when the predetermined criteria is met, or if there is an absence of signal, which may indicate a dead battery or other malfunction. For example, if the pulse rate of the individual wearing the monitoring device 12 reaches a certain predetermined level, the monitoring device automatically communicates with at least one receiver 38, alerting at least one monitoring personnel of the change in pulse rate. It may be desired that the communication only occur when more than one physiological characteristic has been detected at a level beyond the baseline level for each physiological characteristic. In addition, the monitoring device 12 may be capable of communicating with at least one receiver 38 if there is no detected physiological characteristic, which may signal that the device has been removed by the individual. The particular criteria for requiring communication with the receiver(s) may be defined by the user, and will be explained in further detail below.

The base station 36 could be a stand-alone device that is capable of containing its own input and output components. In another embodiment, it may be a hand-held or table-top device that interfaces with a desktop/laptop computer, for example, via a USB port. In yet another embodiment, the base station 36 may be a device installed directly into the circuitry of a personal computer.

In one implementation, the base station 36 includes a wireless communication means that employs wireless technologies, such as Zigbee radio technology. As noted above, the monitoring device 12 may contain a radio frequency (RF) transmitter and antenna for this purpose.

The system 10 for monitoring patients to detect sentinel events further includes an alert device 54 to be worn by staff at the facility, for example. The alert device 54 includes a receiver 56 which receives signals from the base station 36

(or in some embodiments directly from the monitoring device 12) when a sentinel event has been determined to have started, and may also receive all-clear signals periodically. In one embodiment, the alert device 54 includes a transmitter 58 that can send status signals to the base station 36, such as automatic signals that everything is operating normally, and permit staff-initiated signals to communicate messages such as that staff is responding, additional assistance is required, or the event is over. Such messages may be digital or analog, and may be encoded, and may be programming instructions, text or audio. These messages can be communicated using spoken or written language or simply be pressing dedicated buttons (virtual or real). In one example, the receiver 56 and the transmitter 58 are integrated to form a transceiver 60.

The alert device 54 further includes a processor 62 connected to a system bus 64. The processor 62 communicates via the system bus 64 with the receiver 56, a computer-readable medium 66 (e.g., memory), and optionally a display 68. In some embodiments the processor 62 is simple and the alert device 54 has only minimal functionality. In some embodiments, the processor 62 is more powerful and allows more complicated interactions between the base station 36 and the alert device 54. The display 68 can show the location of the sentinel event and its status, plus optionally a timer (not shown) indicating how long it has been since the event started. Information may also be communicated verbally, and speech recognition software can be used to interpret spoken communications.

The alert device 54 may further include a visible, audible, or tactile (or any combination thereof) signal generator 70 connected to the processor 62 to let the staff know through light, vibrations or sound (including speech) when there is an alert due to a sentinel event.

The alert device 54 further includes a power source 72 to supply power to all the components. It can be of the same type as those used for the patient-worn monitoring device, for example.

In some embodiments, the alert device 54 incorporates a tracking or location device 74 which can indicate or determine the location of the alert device. In these embodiments, the alert device 54 transmits its location periodically to the base station 36. The base station 36 can use location information to determine which staff member is closest to where the event is occurring, and also to track the response of the staff.

In one embodiment, the functionality of the alert device 54 is incorporated into a legacy device, such as a pager, phone, or a communication device such as a Vocera B3000 Communication Badge. Alert information can be communicated verbally via a speaker in the legacy device or through a text or multimedia message. In one embodiment, the alert device 54 is a smart phone with a custom application that would provide all the optional functionality described above. The smart phone may operate over an open or closed telecommunication network.

In one embodiment, the alert device 54 includes a one-way radio capable of receiving a voice message from the base station. In one embodiment, the alert device 54 includes a two-way radio capable of sending signals to and receiving signals from the base station.

Figure 2:
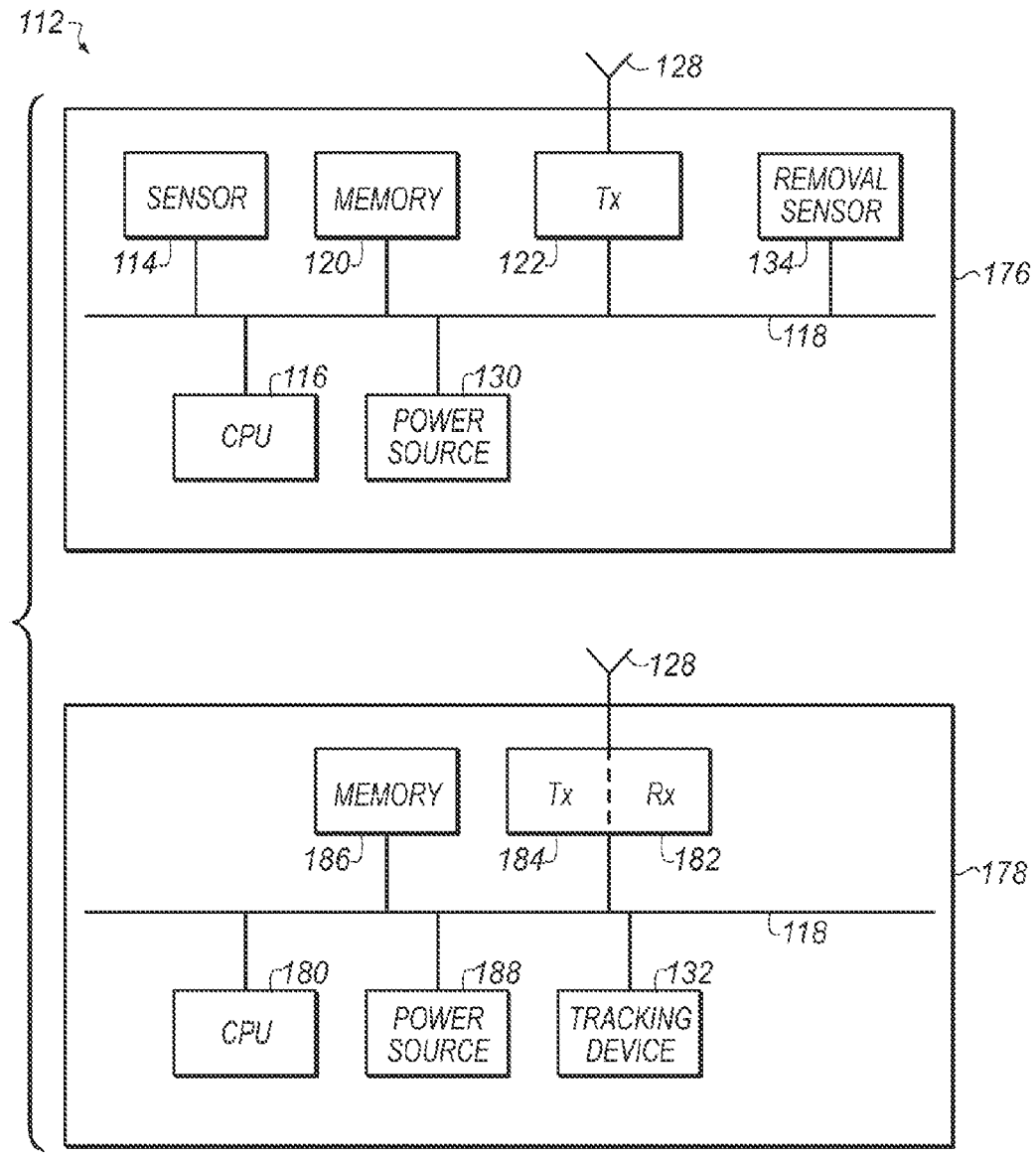
FIG. 2 depicts an alternate embodiment of the monitoring device of FIG. 1.

Turning now to FIG. 2, wherein like numerals indicate like elements in FIG. 1, an alternate embodiment of the monitoring device 112 is depicted. The patient-worn monitoring device 112 has two parts, a patient-worn sensor unit 176 and a patient-worn relay unit 178. This configuration reduces the transmitting load on the patient-worn sensor 176 by reducing the distance its signals need to be transmitted, thereby conserving power. Instead of transmitting to a receiver connected to the base station which could be tens or hundreds of feet away, the transmitter 122 of the patient-worn sensor 176 need only transmit to the patient-worn relay unit 178 which could be within six feet, and most likely closer than three feet. The relay unit 178 can include a processor 180 to process the information in the signal from the patient-worn sensor 176 to determine whether a sentinel event has started, and if so, can transmit a stronger signal to reach one of the base station's receivers. Short-range, low-power transmitting protocols can be used.

The patient-worn sensor unit 176 can incorporate all of the components of the patient-worn monitoring device depicted in FIG. 1 except the tracking device. That is, the sensor unit 176 may include a sensor 114 comprising a pulse sensor and an oximeter (or a pulse oximeter), a processor 116, optionally connected to a memory 120, a transmitter 122, a power source 130, and a removal sensor 134. As noted above, the pulse-oximeter can be used to detect removal, although it may be preferably in some cases to use a separate removal detector to conserve power). The processor 116 can have relatively low computational power because any computationally intensive processing can be done by a processor 180 in the patient-worn relay unit 178 with its bigger power supply. A tracking device 132, if there is one, can be in the patient-worn relay unit 178. Only the patient-worn sensor 176 need be ergonomically or otherwise adapted for wearing above the neck, for example hooked on or otherwise supported by the ear, or in a band or hat for sensing on the forehead.

The patient-worn relay unit 178 may include a receiver 182 adapted to receive transmissions from the sensor 176, and a transmitter 184 adapted to transmit data to the base station 36 (these can be combined in a single transceiver). The patient-worn relay unit 178 may further include a processor 180 with memory 186; a power source 188 (which can be any of those listed above); and a tracking device 132 for determining the location of the relay unit 178. The functionality of the patient-worn relay unit 178 can be incorporated into the operation of a communication device such as a Vocera B3000 Communication Badge, such as by either incorporating in the device an additional receiver tuned to receive the transmissions of the patient-worn sensor unit 176 or incorporating into the patient-worn sensor a transmitter 122 capable of transmitting at a frequency the device can successfully receive.

While the patient-worn sensor 176 is still worn above the neck in one of the locations already indicated, the relay unit 178 can be worn by the patient anywhere on his or her body, such as in an arm or wrist band, on a belt, on a lanyard around the neck (preferably to one that cannot be used as a ligature), clipped to clothing, or as an ankle bracelet, or in any of the ways people carry pagers, cell phones or portable music players. In these locations the weight of a larger battery will be more comfortably borne than in an ear piece, so the power supply can be larger and heavier and have greater capacity. In one embodiment, the sensor 114 incorporates only a pulse sensor and the relay unit 178 incorporates an oximeter (such as the WristOx made by Nonin). By splitting the power load between the patient-worn sensor and the patient-worn relay, the time between recharging for the power sources of both devices can be extended. Another advantage is that the range of the transmitter for the patient-worn relay can be significantly greater than that of the patient-worn sensor due to the greater power available to it. Moreover, different wavelengths can be used by the two transmitters, with the benefit that the relay's transmitter 184 can optionally operate at a wavelength better able to transmit through building structures or long distances, and the sensor transmitter 122 can optionally operate at the wavelength requiring the lowest power or at one for which transmitters are inexpensive, or are small and light. Using separate frequencies also eliminates any interference between sensor and relay transmissions. The relay's receiver 182 may receive signals at a third frequency.

Power transfer between the patient-worn relay 178 and the patient-worn sensor device 176 can be made possible using resonant inductive coupling to transfer energy between a resonant circuit built into the relay device and a resonant circuit built into the sensor device that are tuned to the same frequency. The frequency chosen must be such that the relay device 178 and the sensor device 176 will be within a fraction of a wavelength of each other so that evanescent wave coupling is achieved and efficiency is around at least 80%. The relay 178 may need to incorporate an inverter to convert the direct current of its battery to an alternating current to drive its resonant circuit and the sensor 176 may need to incorporate a rectifier to convert the alternating current from its resonant circuit into direct current. In this embodiment, the sensor device 176 may draw all its power from the relay unit 178 through the resonant inductive coupling, thereby eliminating the need for its battery, or the power transferred to the sensor device 176 may be used to continually or periodically charge its battery, thereby allowing either a reduction in battery size and weight or an extended time between chargings. The relay unit 178 has fewer constraints on size and weight than the sensor unit 176 and therefore its battery can be larger and heavier, sufficiently so to provide power for both units.

In another embodiment of the two part patient-worn monitoring device 112, patient-worn sensor assembly 176 can be attached by wire or optical fiber to the patient-worn relay assembly 178. In this embodiment, components that are shown in FIG. 2 as being in the patient-worn sensor device 176 can be in the relay device 178, including the processor 116, memory 120, transmitter 122, and power source 130. If there is an optical fiber connection, the LED and light detector of a pulse-oximeter sensor 114 can be part of the relay assembly 178, with the fiber carrying light from the LED to the ear (or scalp or forehead) and carrying reflected or otherwise transformed light signal back from the ear (or scalp or forehead) to the light detector.

In order that the patient-worn monitoring device or sensor unit can continually operate as long as possible with as compact and light a power supply as possible, several power saving schemes can be used. As suggested above, transmissions may occur only when a sentinel event is detected, or only periodically, such as once every three or five minutes, except when the removal sensor detects that the patient has removed the device. The pulse-oximeter uses significant power and it may be turned on only periodically as well, preferably coordinated with the transmission cycle. The length of these periods can be set at the factory based on calculations as to what duty cycles are optimal or those operating the system may be able to set them to be consistent with the facility's needs. The duty cycles may even be randomized, so that the time between transmissions can vary. It takes time for a pulse-oximeter to start accurately sensing the pulse and oxygenation level after it is started, and this delay must be considered when setting a duty cycle for the pulse-oximeter sensor. The time between turning the physiological characteristic sensor (e.g., pulse-oximeter) off and on can fluctuate based on other information available to the monitoring devices processor. For example, the monitoring device may also incorporate additional sensors connected to the processor, such as a skin-conductance sensor or an inertial sensor, that can provide additional information about the wearer which can be used to determine when to turn on the pulse-oximeter or other sensor. For example, it may be found that an individual's skin conductivity increases (such as due to increased perspiration) immediately prior to a suicide attempt, and therefore any sudden increase in skin conductivity detected by the appropriate sensor would indicate a need to immediately activate the pulse-oximeter. Alternatively, it may be learned that when a person's body above the neck is stationary or moving in a linear manner (such as when sleeping or watching TV, or when walking), that person is unlikely to be attempting suicide, and conversely, when there is are sudden changes or certain types of movements detected by an inertial sensor, the likelihood of suicide is greatly increased. This information from the inertial sensor would be used to trigger an immediate turning on of the pulse-oximeter.

Figure 3:
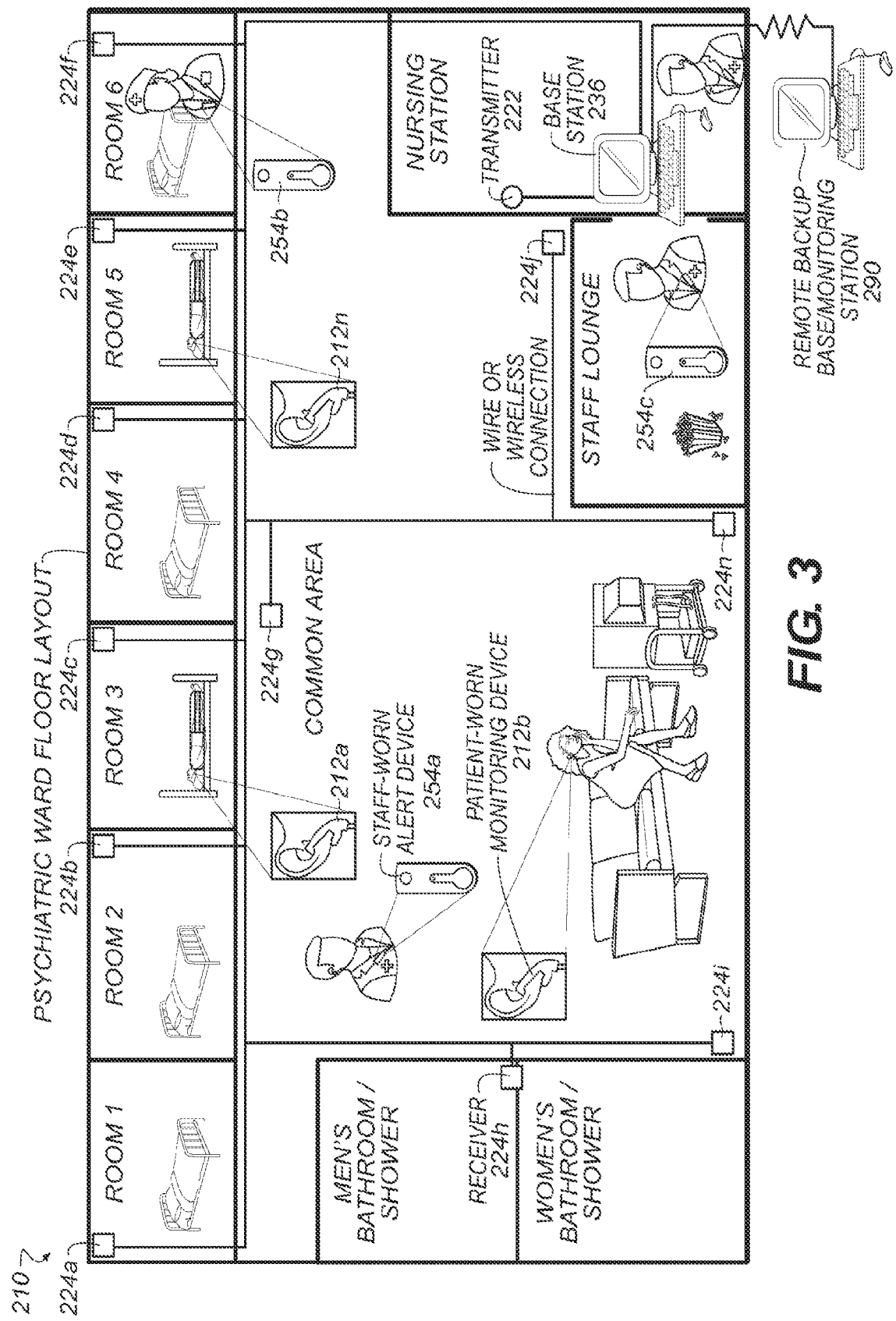
FIG. 3 depicts an exemplary embodiment of a system for detecting a sentinel event in accordance with the present invention.

Turning now to FIG. 3, wherein like numerals indicate like elements in FIG. 1, shown is a possible implementation of a system 210 for monitoring for sentinel events. The system 210 includes a set of receivers 224a-224n located at various points around the facility and connected either by wires or wirelessly to a base station 236. The system 210 further includes a transmitter 222 (or transceiver) connected to the base station 236 either by wires or wirelessly.

The system 210 further includes a plurality of patient-worn monitoring devices 212a-212n and a plurality of staff-worn alert devices 254a-254n. The base station 236 or optionally the patient-worn monitor 212 comprise software for evaluating the data provided by the sensor component of the patient-worn monitor and determining when a predefined sentinel event has occurred. The number and location of the receivers 224 is determined by the needs of the system—there should not be any dead zones where the transmitted signal from a patient-worn monitor cannot reach enough receivers that its location can be determined and its data transferred successfully. More receivers will be necessary in facilities with thick walls that occlude transmissions than in a facility with wooden stud and sheetrock construction. If triangulation of the radio signal is used for location determination, then generally at least three receivers must be able to receive the signal from the patient-worn monitor. Transmission can be done by a single sufficiently powerful transmitter or by multiple transmitters, such as for example in the case where some or all receivers also incorporate a transmitter. Power is supplied to all components of the system requiring power by an appropriate means, such as fuel cell, battery, power grid, solar, inertial power generator, induction, etc.

The base station 236 may optionally be connected by some means (e.g., wirelessly, wired) to a remote backup monitoring station 290 which may replicate some or all functionality of the base station described here. In one embodiment, the remote backup monitoring station 290 receives data via the base station transceivers, processing the data in the same manner as the base station. In other embodiments, the remote backup monitoring station 290 receives a raw data stream from the monitoring device(s) 212, and in other embodiments may simply echo the local base station 236.

Location determination can be done in other ways such as by using RFID tagging technology used to secure and track products, or by using GPS technology. Passive, active and power-assisted RFID technology can be used. If passive tags are used, the passive RFID tag can be incorporated into a patient-worn device (monitor, sensor or relay), with fixed RFID readers located at strategic points around the facility, or the reader can be incorporated into a patient-worn device and passive RFID tags can be located at strategic points around the facility. Fixed RFID readers incorporated into or attached to the walls or ceiling of each room of the facility can draw power from the grid and may be sufficiently powerful to identify all patients (i.e., all patient worn devices incorporating an RF ID tag) within that room (some large rooms might need more than one reader). If the RFID tag in the patient-worn device is powered by the interrogating signal from the RFID reader, excess power received from the readers can be diverted to charging a battery-power source for the patient-worn device. In one embodiment, RFID readers and the receivers are incorporated into a single device, simplifying installation of such a system. In either case, the patient's location is determined by the known location within the facility of the RF ID tag being read or the reader doing the reading (or last read or doing the reading). If a patient's location cannot be detected for more than a certain amount of time (e.g., 5 seconds, 20 seconds), an alert may be triggered.

Figure 4:
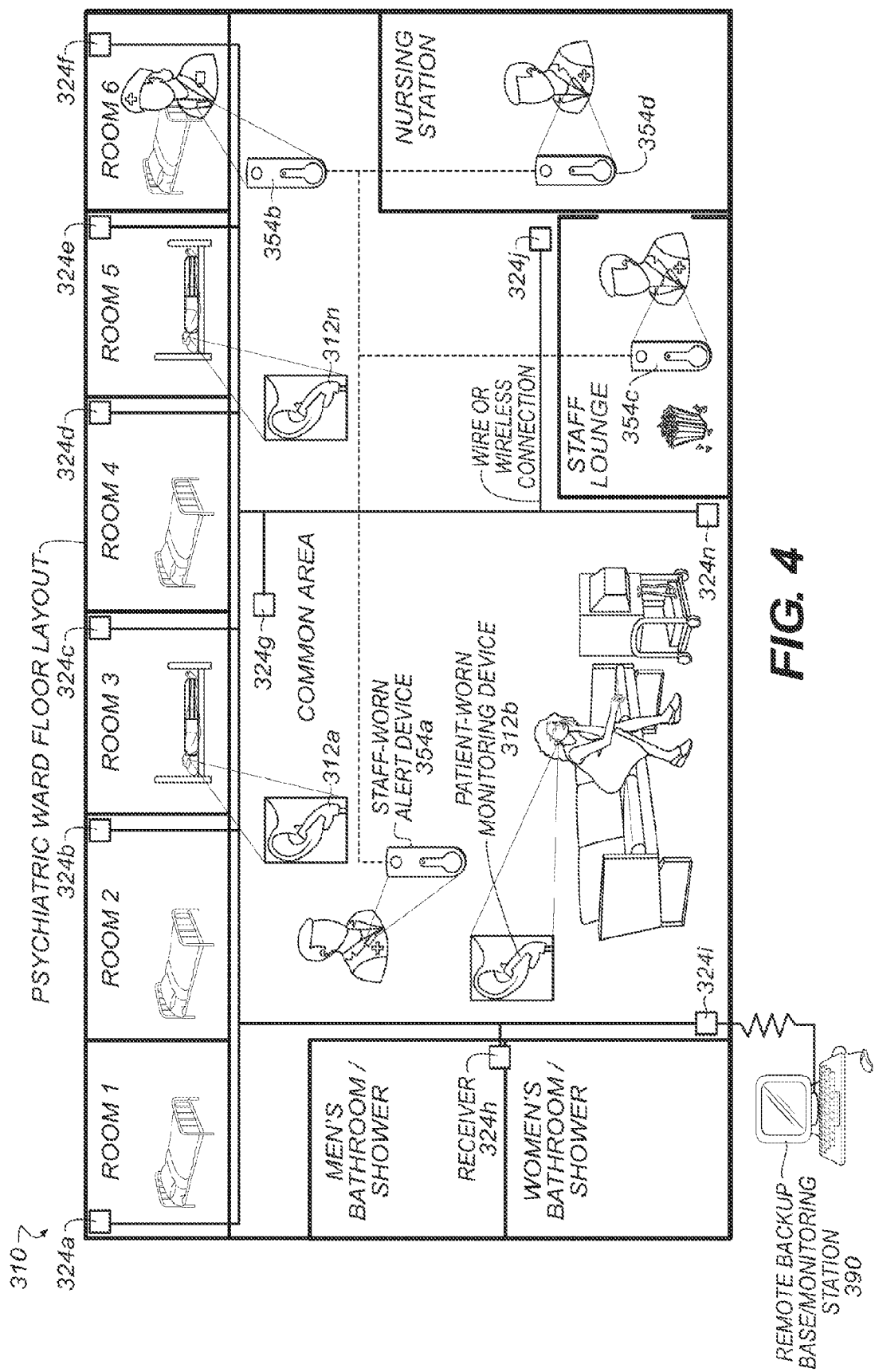
FIG. 4 depicts another exemplary embodiment of a system for detecting a sentinel event in accordance with the present invention.
Figure 5:
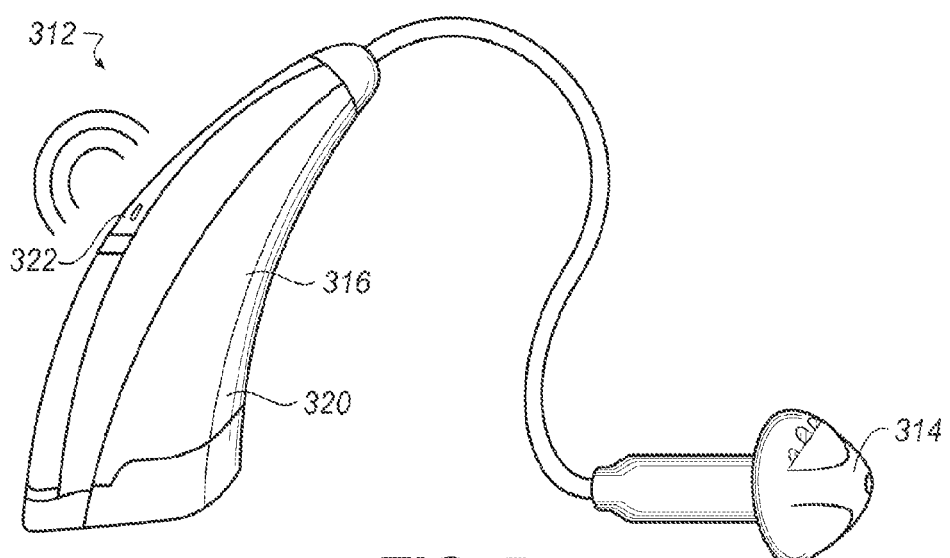
FIG. 5 depicts an exemplary monitoring device according to one embodiment of the present invention.
Figure 6:
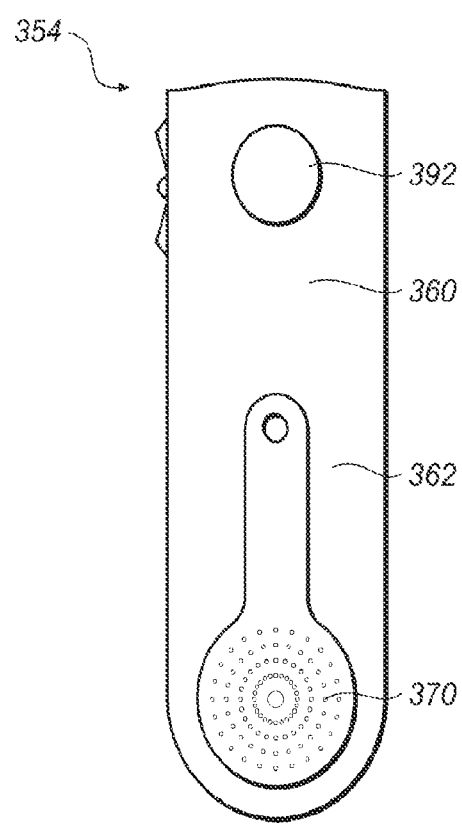
FIG. 6 depicts an exemplary alert device according to one embodiment of the present invention.

Turning now to FIGS. 4-6, wherein like numerals indicate like elements in FIG. 1, shown is another implementation of a system 310 for monitoring for sentinel events. The system 310 includes at least one monitoring device 312; in the illustrated embodiment a plurality of patient-worn monitoring devices 312a-312n are shown. The system 310 further includes at least one alert device 354; in the illustrated embodiment a plurality of staff-worn alert devices 354a-354n are shown. The system 310 may further include at least one repeater 392, realized in the form of a transceiver unit. The system 310 may further include a remote backup monitoring station 390. The monitoring device 312 is intended to be worn by an individual considered at risk of some sentinel event, such as suicide. The monitoring device 312 incorporates a sensor 314 capable of detecting at least one physiological characteristic, including heart rate, pulse rate, pulse amplitude, presence of a pulse, and oxygen levels in the blood of an at-risk individual. An example of such a sensor is a pulse oximeter, which is capable of detecting the oxygen levels in the blood of the individual. The monitoring device 312 is adapted for wearing above the neck so that the physiological characteristic is sensed above the neck. The monitoring device 312 also incorporates a transmitter 322 and a processor 316 connected to both the sensor and the transmitter which is capable of transmitting a signal, continuously or periodically, to a receiver that is incorporated into the alert device. The monitoring device 312 also optionally incorporates a tracking device and/or a separate removal sensor (not shown). The processor 316 may be programmed to process the data received from the sensor 314 to determine whether a sentinel event has begun or is occurring. The processor 316 optionally has a memory 320 for storing information on the wearer (such as baseline physiological data) or other information useful to identifying sentinel events. The monitoring device 312 may be termed a "smart" device in that it may be programmed to 'learn' as it is being used and to either create or modify the baseline physiological data based on past sensor data. When a sentinel event is detected, the processor 316 will create and effect the transmission of an alert to the alert device(s) 354. The signal sent may also indicate the device's location.

The alert device 354 is intended to be worn by staff. It incorporates a transceiver 360, an alert mechanism 370 (audible, tactile, visual, etc.), and a processor 362. It optionally incorporates a tracking device (not shown).

The system 310 may incorporate one or more repeaters 392 which receive and retransmit signals from a monitoring device 312 to an alert device 354, and optionally signals between two or more alert devices. The repeater 392, realized as a transceiver in the illustrated embodiment, is capable of receiving signals from the monitoring device 312 (directly or via a repeater) and from other alert devices 354n, and as a result, alert devices are capable of communicating with one another, as illustrated by the dashed lines. This capability allows the staff wearing the devices to coordinate their response to an alert signal. The alert devices can form an ad hoc network, relaying any signal received to all other alert devices within range, or operate like two-way radios sharing a single frequency, which may be a different frequency than that used to transmit alerts.

Thus, in at least one embodiment, the system consists of (a) monitoring devices worn by at-risk individuals above the neck which monitor their physiological characteristics using a sensor or sensors, analyze the sensor data to determine whether a sentinel event is occurring (optionally utilizing the individual's own or some typical baseline levels for the physiological characteristics stored on the device in the analysis), optionally determine its location and, when a sentinel event is detected, transmit an alert to the alert devices; and (b) alert devices worn by staff which receive the alert signal, and optionally the location of the alert, alert the wearer through some tactile, visual or auditory signal, communicate the location of the alert if it is communicated, and allow staff wearing the devices to communicate with each other to coordinate a response, preferably allowing voice communication. The monitoring device or the alert device may keep track of the time elapsed from the beginning of an alert, and this time can be indicated on the alert device by a recorded message (e.g., "one minute has passed since the alert"), display, or special lights (for example, a lighted bar which starts fully lit and gets progressively smaller as the time before permanent injury may occur).

To discourage the removal of the monitoring device by the wearer and potentially for the purpose of letting the wearer know that staff is going to come to him or her, the monitoring device may optionally incorporate an auditory signaling device or alarm that will go off immediately or within a predetermined time after an alert is detected (e.g., 0 seconds, 5 seconds, 10 seconds, 20 seconds) or the device is removed.

The alarm can be loud to help draw attention to the event and perhaps make it easier for staff to find the at-risk person. In one embodiment, the alarm is replaced by a receiver that allows staff to speak directly to the at-risk individual. This allows staff to tell a person to put the device back on if the removal sensor detects that it has been removed, or tell a person who is deemed to be undergoing a sentinel event that help is on its way and offer encouragement, or even enable staff to try to talk a person committing suicide into ending the attempt even before the staff can get to the location.

In one embodiment of the present invention, a method of detecting and responding to a sentinel event includes securing the monitoring device 12 to the at-risk individual, most desirably at a location above the neckline, such as the ear or behind the ear. This monitoring device 12 is activated, and at least one physiological characteristic is measured. The method includes establishing a criterion for each physiological characteristic that, if met, will cause an alert to be initiated. In other words, the method could include setting a baseline level for at least one characteristic for the at-risk individual, the baseline being the level of the physiological characteristic in a normal state. For example, if the physiological characteristic to be measured is pulse rate, the pulse rate of the at-risk individual in a normal setting is measured and set as a "baseline" level. Any combination of physiological characteristics may be monitored, and desirably the baseline level for each characteristic is set. The criterion can be stored in the memory of the monitoring device. It is important that the monitoring device be assigned to and set for the particular at-risk individual who will be wearing the device, as baseline levels for various physiological characteristics differ among individuals.

The method continues by leaving the monitoring device attached to the at-risk individual and monitoring the at least one physiological characteristic. Any physiological characteristic or characteristics may be monitored, either continuously or periodically. The monitoring device measures the at least one physiological characteristic and a processor analyzes the currently measured level with the baseline or criterion level for that individual. The computations may be carried out by a processor in the monitoring device or a base station, for example.

The monitoring device is programmed to monitor the at least on physiological characteristic for changes, and compare the changes to the programmed baseline level. The monitoring device is programmed to determine whether at least one monitoring personnel needs to be notified of the change in the at least one physiological characteristic. In one embodiment, the monitoring device is programmed to send an alert when the measured level for at least one physiological characteristic differs from the baseline level by a certain predetermined amount. For example, if the pulse rate of the individual changes from the baseline about 15-20 beats per minute or drops below 50 or rises above 120 beats per minute, then the monitoring device will send an alert, as will be explained in further detail below. Similarly, if the measured blood oxygen saturation drops to 5% below the baseline level or to 90% or below (absolute value), then monitoring device may send an alert.

In some embodiments, the monitoring device may only measure for one particular physiological characteristic, while in other embodiments, it may measure for a plurality of physiological characteristics. It may be desired that the alert be only sent when more than one physiological characteristic differs from the baseline level for each physiological characteristic by a certain predetermined amount. For example, the monitoring device may only send an alert when the pulse rate differs by a certain level and the blood oxygen level differs by a certain level. By requiring a difference in the level for at least two physiological characteristics, the monitoring device may more accurately detect dangerous conditions and reduce the possibility of false alarms. Any combination of physiological characteristics may be used as desired.

At least one receiver is provided, the receiver capable of communicating with the monitoring device. There may be one central receiver, or there may be a plurality of receivers. Desirably, the receiver and the monitoring device communicate wirelessly, but other known forms of communication are useful. The receiver also desirably includes a means of displaying information related to the particular monitoring device that is communicating with the receiver. For example, the receiver may include a visual display, an audible speaker, or any other means of displaying information. The receiver or receivers may be hand-held and/or portable, to allow for continuous monitoring.

When the monitoring device senses a change in the at least one physiological characteristic that differs from the baseline level by the predetermined amount, the monitoring device sends an alert to at least one receiver. As explained above, the alert is desirably sent wirelessly but may be sent in any known fashion. The alert may communicate any information to the receiver(s) desired, and in preferred embodiments the alert provides enough information to allow at least one monitoring personnel to check on the at-risk individual in a timely and efficient manner. For example, the monitoring device may communicate the name of the individual, identifying physical characteristics of the individual, the location of the individual, the change in the at least one physiological characteristic, and combinations thereof. It is particularly useful if the monitoring device includes a tracking device, capable of communicating the exact location of the at-risk individual to the receiver(s). For example, the monitoring device may be capable of determining the precise room in which the monitoring device is located, and communicate that precise room to the receiver(s). The communication should occur as quickly as possible, and in desired embodiments in less than 5 seconds.

Finally, when the receiver(s) receive the alert, and any information that may optionally be provided with the alert, at least one monitoring personnel responds to the alert. In embodiments where the receiver is at one central location, there is desirably at least one monitoring personnel in the vicinity of the one receiver, and capable of detecting the presence of the alert. In some embodiments, there may be a plurality of receivers and a plurality of monitoring personnel, where each monitoring personnel has an individual receiver capable of communicating with the monitoring device. The monitoring device sends the alert to the at least one receiver, where the monitoring individual(s) receive the alert and can act accordingly. In some embodiments, the monitoring individual may personally check on the at-risk individual in person, while in other embodiments, the monitoring individual may review one or more video monitors or audio devices (not shown) to check on the individual. In other embodiments, the monitoring individual may direct other monitoring personnel to check on the individual. In some embodiments, particularly when the nature of the alert is communicated to the receiver and the monitoring personnel is aware what physiological characteristic is being compromised, the monitoring personnel can act accordingly for the particular physiological characteristic. For example, if alert is sounded because of a drop in heart rate, the monitoring personnel may be equipped with a defibrillator or other device that may be required. In some embodiments, the monitoring personnel may provide medications to the individual. In some embodiments, the monitoring personnel may simply be equipped with a stethoscope or other monitoring device to diagnose the individual. In preferred embodiments, the monitoring personnel is equipped with a knife or blade to cut a ligature in a hanging attempt. Most desirably, the monitoring personnel is capable of preventing death or serious bodily injury to the individual if the need arises.

There may be one receiver or set of receivers that is part of a base station which relays the alert to a second set of second receiver worn by staff. The receivers worn by staff may be as described in detail above. The base station may also incorporate a display for displaying information about each monitoring device, such as its current location, state and the level of the physiological characteristic(s) or parameter(s) being monitored. The receivers worn by the staff may also incorporate a transmitter for communicating back to the base station through its receiver or receivers information about the staff member or, during an alert, the status of the response, information that may also be displayed by the base station.

It is particularly desired that the response by the monitoring personnel occur as soon as possible. For example, when an individual attempts hanging, that individual often suffers from severe physical harm within about 3-6 minutes. Desirably, the monitoring personnel may respond in a time frame that is less than the time it takes to suffer severe physical damage. Thus, in desired embodiments, the entire method takes less than 3-6 minutes to complete. In more preferred embodiments, the entire method takes less than 2 minutes to complete, or less than 1 minute to complete. That is, the time the change in physiological characteristic(s) is detected to the time the monitoring personnel takes action should be less than 3-5 minutes, less than 2 minutes or less than 1 minute. In preferred embodiments, the method is completed by stopping the sentinel event from occurring to completion and/or by reducing the likelihood of physical harm from occurring.

In another embodiment of the present invention, there is provided a monitoring device to be worn by at-risk individuals, a receiver or receivers connected to a base station, and an alert device to be worn by staff in the facility providing custodial care to such at-risk individuals. The monitoring device is configured and operates as described above.

In this embodiment, there is provided at least one receiver, capable of receiving communications from the monitoring device, which is connected electrically, wirelessly or otherwise to a monitoring base station. The base station is configured as described above.

In one embodiment, the monitoring device sends un- or partially processed data to the base station and does not itself determine and communicate to the base station whether a sentinel event has begun, the processor at the base station will analyze such data and determine the state of the patient. Upon certain predetermined criteria being met, the base station will determine that a sentinel event is occurring and will transmit an alert signal to the alert devices worn by staff. For example, if the pulse rate of the individual wearing the monitoring device reaches a certain predetermined level, the base station automatically communicates with at least one alert device, alerting at least one monitoring personnel of the change in pulse rate. It may be desired that the communication only occur when more than one physiological characteristic has been detected at a level beyond the baseline level for each physiological characteristic. In addition, if there is no detected physiological characteristic, which may signal that the device has been removed by the individual, the base station may transmit an alert. Some monitoring devices may incorporate sensors to detect removal of the monitoring device from its location on the at-risk individual, and will communicate to the base station whenever the device is so removed so that an alert can be transmitted from the base station to the staff-worn alert devices.

The monitoring device may incorporate a tracking device, such as a GPS (global positioning system) device, capable of determining its location periodically or continuously, and this information may be transmitted to the base station along with or separately from physiological data obtained by the sensor(s) sensor in the monitoring device. Alternately, the base station may be able to determine the location of each monitoring device by using a signal originating from it, such as a dedicated tracking beacon or the signal transmitting sensor data, or by other means such as an embedded RFID tag. This location information will preferably be transmitted to staff via the alert device, along with information about the sentinel event, such as its type, severity and who is involved.

Tracking information provided by the monitoring device giving the location of the patient or inmate can also be used determine when a patient or inmate has entered certain areas of the facility. Specific areas of the facility can be pre-designated as areas where there is a higher risk of a suicide being attempted, areas where a patient or inmate would not be expected to tarry long, such as in a closet or behind a door, areas which are officially off limits to the individual. When a patient or inmate is detected as entering into one of those areas, a suitable alert can be sent to staff, such as, for example, go check on inmate A who is in the closet of his room, or patient B has left the ward, bring her back. The location of all monitoring device wearers could be indicated on a map on a display screen at all times, such as a display screen at a base station, or accessible from any staff computer.

In either embodiment described above there may be a remote monitoring station attached to the receivers or the base station. A remote monitoring station provides backup for the on-site system and personnel, and can facilitate the coordination of any response. Many facilities where the present invention have bare-bone levels of staffing and a remote monitoring station can help make sure that there is a response to every alert. The method would include the steps of communicating alerts, and preferably the status of each individual wearing a monitoring device, to the remote monitoring station, and monitoring the response to any alert.

As explained above, the present invention is not limited to suicide attempts, and may be applicable in any number of events in which one or more physiological characteristics is changed above or below a certain baseline level. For example, the invention may be used to monitor and respond to likely panic attacks, in which the at-risk individual's pulse rate is greatly increased during the attack. The method steps outlined above are applicable in this embodiment. In the case of panic attacks, the heart rate and pulse rate will rapidly increase, and thus the monitor desirably checks for changes in at least one of these characteristics above the baseline. When the characteristic(s) is above the baseline by a predetermined amount, the alert is activated and at least one monitoring personnel may act accordingly, as explained above.

The present invention may also be useful in the case of potentially harmful drug use, including psychiatric drugs and drugs of abuse, where at least one physiological characteristic is modified when drugs are being taken. Different drugs have different effects on physiological characteristics, and thus the monitor may be capable of determining whether changes to the characteristic(s) evidencing use of any particular drug are occurring. As with above, the alert is activated and at least one monitoring personnel may take action.

The present invention may be useful for use with the elderly, such as in a retirement home or other nursing facility. The sentinel event may be, for example, a heart attack or stroke. As with the other events, these events have an effect on at least one physiological characteristic, which may be monitored against that particular at-risk individual's baseline levels, and sending an alert when a particular change is noticed. The at least one monitoring personnel may respond accordingly.

The present invention provides many benefits, not the least of which is the ability to prevent death and/or serious bodily harm to an at-risk individual by providing quick and accurate response by at least one monitoring personnel. The ability to continuously monitor at-risk individuals without having to rely upon constant in person supervision by personnel saves tremendous cost and time. Further, reliance upon human observation has inherent defects, even when human observation is continuous, whereas reliance upon technology provides more accurate and more constant observation. Even further, typical personnel observation is conducted on a regular basis, such as every 10-15 minutes, which therefore gives 10-15 minutes where the at-risk individual is not being personally monitored. Serious injury or death may occur in as little as 3 minutes, and thus more constant monitoring is desired. The present invention provides not just regular observation, but continuous observation of the at-risk individual.

In addition, the present invention allows for continuous or intermittent monitoring of the individual even in "private" settings, such as bathrooms, where observation by human personnel is not always provided. The present invention allows even the most "at-risk" individuals to have privacy and freedom from direct human observation during moments when such privacy is desired.

The present invention may additionally provide psychological benefits to the at-risk individuals beyond the physical benefits achieved through the actual monitoring and response steps. Use of the monitoring system has the benefit of making the at-risk individual feel safer, with the knowledge that there is continuous monitoring and protection of him at all times. This may make at-risk individuals feel more secure, and thus less likely to attempt a sentinel event such as suicide, taking drugs, or suffering a panic attack. In addition, use of the present invention may provide the feeling to such at-risk individuals that the personnel in charge of the custodial care setting "care" about the individual, making that individual feel better and thus less likely to attempt suicide. Taken together, the use of the present invention may reduce the likelihood that an attempted event may take place at all. However, if the event does take place, the present invention is capable of preventing a harmful result of that event from occurring.

Sleep Situation

An individually worn earpiece may not be suitable or comfortable during sleep for all patients. In some cases, an alternative sleep-worn sensor device, with the same components, may be used. The components, as described above, could be placed into an alternative means of affixing to one's body above the neckline. For example, the monitoring device may be attached to headwear, such as a stocking cap, hat, or headband.

Alternatively, a sensor device could be attached to an alternate site on the body of the individual, such as the finger, wrist, or chest, for example. If this were to be the case, in order to detect a hanging event, there would need to be an additional component, such as a gyroscope or accelerometer, to provide information on the individual's posture. Since a hanging attempt, which would only be detectable by the absence of a pulse above the neck, would necessitate an upright or reclined posture, the posture detection device could signal an alert if the individual did not maintain a recumbent posture.

For the purpose of obtaining additional data on the health status of the at-risk individual, additional sensors can be placed in other anatomical locations of the wearer of the sensor. The purpose of this data would be to: (1) confirm data from above the neck monitor, (2) provide backup physiologic monitoring should the primary monitor fail, (3) provide a ratio of physiologic parameters at different anatomical sites which correlates with specified pathological states, and (4) provide physiological data specific to the site of sensor placement (e.g., ankle monitor would show if leg was amputated). Potential anatomical locations of additional sensors include, but are not limited to, wrist, fingers, arm, waist, legs, ankle, feet, and toes.

A sample of systems, methods, and devices that are described herein are as follows:

1. A method of preventing a sentinel event by an at-risk individual, wherein said at-risk individual is maintained in a custodial care setting, comprising the steps of:

securing a monitoring device to said at-risk individual above the neckline of said at-risk individual, wherein said monitoring device is capable of collecting data on at least one physiological characteristic selected from the group consisting of pulse amplitude, heart rate and blood oxygen saturation of said at-risk individual;

for each at least one physiological characteristic, determining a process for analyzing the data collected on each at least one physiological characteristic by said monitoring device and establishing a criterion that if met will cause an alert to be initiated;

monitoring said at least one physiological characteristic of said at-risk individual;

analyzing the data collected by said monitoring device on each at least one physiological characteristic to determine if said criterion for initiating an alert has been met; and initiating an alert when said criterion has been met for said at least one physiological characteristic, including alerting at least one monitoring personnel.

1A. The method, further comprising the step of said monitoring personnel responding by checking the status of said at-risk individual.

1B. The method, wherein said the step of determining a process for analyzing the data collected and establishing an alert criterion comprises the steps of (i) setting forth a baseline level for said at-risk individual for said at least one physiological characteristic, wherein said baseline level is the level of said at least one physiological characteristic in a normal state; and (ii) setting a pre-determined amount by which if said at least one physiological characteristic differs from said baseline level, an alert will be initiated.

2. The method, wherein said sentinel event is attempted suicide.

2A. The method, wherein said at least one physiological characteristic is pulse amplitude.

2B. The method, wherein said at least one physiological characteristic is blood oxygen saturation.

3. The method, wherein said monitoring device is secured to the ear of said at-risk individual.

4. The method, wherein said monitoring device is attached behind the ear of said at-risk individual.

4A. The method, wherein said monitoring device is inserted at least partially into the ear canal of said at-risk individual.

4B. The method, wherein said monitoring device is clipped to the ear lobe.

4C. The method, wherein said monitoring device is secured in the concha of the ear.

4D. The method, wherein said monitoring device is attached to or incorporated into a hat or headband.

5. The method, wherein at least two physiological characteristics are monitored.

5A. The method, wherein said at least two physiological characteristics are pulse amplitude and blood oxygen saturation.

6. The method, wherein said step of alerting occurs when at least two physiological characteristics differ from their respective baseline levels by a predetermined amount.

6A. The method, wherein said step of alerting occurs when one of said at least two physiological characteristics differs from its respective baseline level by a predetermined amount.

7. The method, wherein said step of alerting occurs when said at least one characteristic falls below said baseline level for said physiological characteristic.

8. The method, wherein said step of alerting occurs when said at least one characteristic falls below said baseline level for said physiological characteristic.

9. The method, wherein said predetermined amount is at least 10% of said baseline level.

10. The method, wherein said physiological characteristic is heart rate, and the predetermined amount is one of a difference of about 15-20 beats per minute between the measured rate and the baseline level, a heart rate that is below about 50 beats per minute, or a heart rate that is above about 120 beats per minute.

11. The method, wherein said physiological characteristic is blood oxygen saturation and the predetermined amount is 5% below the baseline level, or is a difference of less than about 90% the absolute value of the baseline level.

12. The method, wherein said custodial care setting is a hospital, psychiatric institution, jail, prison, juvenile detention center, assisted living facility, group home, rehabilitation facility, or nursing home facility.

13. The method, wherein said monitoring device further comprises a tracking system.

13A. The method, wherein the step of alerting said at least one monitoring personnel includes communicating to said at least one monitoring personnel the location of said monitoring device.

13B. The method, wherein the step of analyzing the data collected by said monitor device includes determining the location of said monitoring device.

13C. The method, wherein the location of said monitoring device is determined by analyzing a signal transmitted by the monitoring device.

13D. The method, wherein said analysis of said signal transmitted by the monitoring device comprises comparing said signal as received by a plurality of receivers.

13E. The method, wherein said analysis of said signal transmitted by the monitoring device comprises triangulating the origination location of said signal.

14. The method, wherein said tracking system is capable of determining where said at-risk individual is located within the custodial care setting.

15. The method, wherein said tracking system is capable of alerting said monitoring personnel as to the location of said at-risk individual within the custodial care setting.

15A. The method, wherein the step of alerting said at least one monitoring personnel further comprises the step of communicating to said at least one monitoring personnel the location of said monitoring device.

16. The method, wherein said tracking system is capable of alerting said monitoring personnel when said at-risk individual enters a designated area.

17. The method, wherein said step of alerting comprises sounding an audible alarm.

18. The method, wherein said step of alerting comprises displaying a visual alarm.

19. The method, further comprising a step of securing an alert device to at least one monitoring personnel; and wherein alerting at least one monitoring personnel comprises sending an alert to said alert device.

19A. The method, wherein said monitoring personnel is equipped with said alert device, and wherein said step of alerting comprises sending an alert to said alert device.

20. The method, wherein said alert comprises an alarm selected from the group consisting of audible alarms, visual alarms, vibrational alarms, and combinations thereof.

21. The method, further comprising a plurality of monitoring personnel, wherein each of said monitoring personnel is equipped with a communication device.

22. The method, wherein said monitoring device includes a storage means, and said monitoring device stores data identifying said at-risk individual.

23. The method, wherein said monitoring personnel is capable of intervening in a suicide attempt.

24. The method, wherein said suicide attempt is hanging.

25. The method, wherein said suicide attempt is asphyxiation.

26. The method, wherein said suicide attempt is severing a blood vessel.

26A. The method, wherein said analyzing of data collected by said monitoring device is performed at a base station.

26B. The method, wherein said analyzing of data collected by said monitoring device is performed by said monitoring device.

26C. The method, further comprising the step of sending data about said at least one physiological characteristic from said monitoring device to said base station.

26D. The method, wherein step (d) comprises the steps of (i) the base station comparing the data about said at least one physiological characteristic received from said monitoring station to the baseline level of said at least one physiological characteristic; and (ii) the base station sending an alert to said at least one monitoring personnel when said at least one physiological characteristic differs from said baseline level by a predetermined amount.

27. A method of monitoring the health status of an at-risk individual, wherein said at-risk individual is maintained in a custodial care setting, comprising the steps of:

(a) securing a monitoring device to said at-risk individual above the neckline of said at-risk individual, wherein said monitoring device is capable of collecting data on at least one physiological characteristic selected from the group consisting of pulse amplitude, heart rate and blood oxygen saturation of said at-risk individual;

(b) for each at least one physiological characteristic, determining a process for analyzing the data collected on each at least one physiological characteristic by said monitoring device and establishing a criterion that if met will cause an alert to be initiated;

(c) monitoring said at least one physiological characteristic of said at-risk individual;

(d) analyzing the data collected by said monitoring device on each at least one physiological characteristic to determine if said criterion for initiating an alert has been met; and (e) initiating an alert when said criterion has been met for said at least one physiological characteristic, including alerting at least one monitoring personnel.

27A. The method, further comprising the step of said monitoring personnel responding by checking the status of said at-risk individual.

27B. The method, wherein said step (b) comprises the steps of (i) setting forth a baseline level for said at-risk individual for said at least one physiological characteristic, wherein said baseline level is the level of said at least one physiological characteristic in a normal state; and (ii) setting a pre-determined amount by which if said at least one physiological characteristic differs from said baseline level, an alert will be initiated.

28. The method, wherein said physiological characteristic is the heart rate of said at-risk individual.

29. The method, wherein said physiological characteristic is the heart rate of said at-risk individual and the predetermined amount is one of a difference of about 15-20 beats per minute between said monitored level and said baseline level, is below 50 beats per minute, or is above 120 beats per minute.

30. The method, wherein said physiological characteristic is blood oxygen saturation and the predetermined amount is 5% below the baseline level, or is a difference of less than about 90% the absolute value of the baseline level.

31. The method, wherein said health status comprises at least one heart malfunction.

32. The method, wherein said heart malfunction comprises a heart attack.

33. The method, wherein said heart attack stems from a panic attack suffered by said at-risk individual.

34. The method, wherein said heart attack stems from said at-risk individual taking a narcotic substance.

35. A system for detecting sentinel events comprising a monitoring device to be worn by a patient, an alert device to be worn by staff, a base station; and computer program instructions;

wherein said monitoring device is adapted for wearing above the patient's neck, incorporates a processor, a transmitter capable of sending a signal to the base station, and a sensor capable of monitoring at least one physiological characteristic selected from the group consisting of presence of a pulse, pulse amplitude, heart rate and blood oxygen saturation of said at-risk individual;

wherein said alert unit comprises a mechanism capable of generating an audible, visual or tactile signal, a receiver capable of receiving a signal from the base station, and optionally a transmitter capable of sending a signal to the base station;

wherein said base station comprises a receiver capable of receiving a signal from a monitoring unit, and optionally from an alert unit, a transmitter capable of transmitting a signal to the alert unit, and a processor; and wherein running said set of computer instructions or programs enables a processor to analyze data from the sensor to determine if a sentinel event has begun or is occurring, the processor running the computer instructions or programs being the processor incorporated into the monitoring unit, the processor incorporated into the base station, or both.

36. The system, wherein the monitoring unit comprises a pulse-oximetry sensor.

37. The system, wherein the monitoring unit is formed so that it can be secured to the patient's ear.

38. The system, wherein said monitoring unit is inserted at least partially into the ear canal of said at-risk individual.

39. The system, wherein said monitoring unit is clipped to the ear lobe.

40. The system, wherein said monitoring unit is secured in the concha of the ear.

41. The system, wherein said monitoring device is attached to or incorporated into a hat or headband.

42. The system, further comprising a remote monitoring station connected to the base station.

43. The system, wherein said instruction set or programs enable a processor to determine the location of the monitoring device.

44. The system, wherein said instruction set or programs run on the processor incorporated into the monitoring unit.

45. The system, wherein said instruction set or programs run on the processor incorporated into the base station.

46. The system, wherein the physiological characteristic monitored by the sensor incorporated into said monitoring unit is pulse amplitude or presence of a pulse.

47. The system, wherein the physiological characteristic monitored by the sensor incorporated into said monitoring unit is blood oxygen saturation.

48. The system, wherein the physiological characteristic monitored by the sensor incorporated into said monitoring unit is heart rate.

49. A system for detecting sentinel events comprising a monitoring device to be worn by a patient, an alert device to be worn by staff, and computer program instructions;

wherein said monitoring device is adapted for wearing above the patient's neck, and incorporates a sensor capable of monitoring at least one physiological characteristic selected from the group consisting of pulse amplitude, heart rate and blood oxygen saturation of said at-risk individual, a processor, and a transmitter capable of sending a signal to the base station;

wherein said alert unit comprises a receiver capable of receiving a signal from the monitoring unit, a transmitter capable of transmitting a signal to other alert units, a receiver capable of receiving a signal from other alert units, a mechanism capable of generating an audible, visual or tactile signal, and a processor; and wherein executing said computer program instructions enables a processor to analyze data from the sensor to determine if a sentinel event has begun or is occurring, the processor running the computer program instructions being the processor incorporated into the monitoring unit, the processor incorporated into the alert unit, or both.

50. The system, further comprising one or more relays for receiving and retransmitting signal from the monitoring unit to the alert units.

51. The system, wherein the monitoring unit comprises a pulse-oximetry sensor.

52. The system, wherein the monitoring unit is formed so that it can be secured to the patient's ear.

53. The system, wherein said monitoring unit is inserted at least partially into the ear canal of said at-risk individual.

54. The system, wherein said monitoring unit is clipped to the ear lobe.

55. The system, wherein said monitoring unit is secured in the concha of the ear.

56. The system, wherein said monitoring device is attached to or incorporated into a hat or headband.

57. The system, further comprising a remote monitoring station connected to the base station.

58. The system, wherein said instruction set or programs enable a processor to determine the location of the monitoring device.

59. The system, wherein said instruction set or programs run on the processor incorporated into the monitoring unit.

60. The system, wherein said instruction set or programs run on the processor incorporated into the base station.

61. The system, wherein the physiological characteristic monitored by the sensor incorporated into said monitoring unit is pulse amplitude or presence of a pulse.

62. The system, wherein the physiological characteristic monitored by the sensor incorporated into said monitoring unit is blood oxygen saturation.

63. The system, wherein the physiological characteristic monitored by the sensor incorporated into said monitoring unit is heart rate.

64. A method of preventing a sentinel event by an at-risk individual, wherein said at-risk individual is maintained in a custodial care setting, comprising the steps of:
   (a) securing a monitoring device to said at-risk individual, wherein said monitoring device is capable of monitoring at least one physiological characteristic selected from the group consisting of pulse amplitude, heart rate and blood oxygen saturation of said at-risk individual;
   (b) setting forth a baseline level for said at-risk individual for said at least one physiological characteristic, wherein said baseline level is the level of said at least one physiological characteristic in a normal state;
   (c) continuously monitoring said at-risk individual for changes in said at least one physiological characteristic;
   (d) alerting at least one monitoring personnel when said at least one physiological characteristic differs from said baseline level by a predetermined amount; and
   (e) said monitoring personnel responding by checking the status of said at-risk individual.

65. The method, wherein said sentinel event is attempted suicide.

66. The method, wherein said monitoring device is attached to the ear of said at-risk individual.

67. The method, wherein said monitoring device is attached behind the ear of said at-risk individual.

68. The method, wherein at least two characteristics are monitored.

69. The method, wherein said step of alerting occurs when at least two characteristics differ from their respective baseline levels by a predetermined amount.

70. The method, wherein said step of alerting occurs when said at least one characteristic falls below said baseline level for said physiological characteristic.

71. The method, wherein said step of alerting occurs when said at least one characteristic is above said baseline level for said physiological characteristic.

72. The method, wherein said predetermined amount is at least 10% of said baseline level.

73. The method, wherein said physiological characteristic is heart rate, and the predetermined amount is one of a difference of about 15-20 beats per minute between the measured rate and the baseline level, a heart rate that is below about 50 beats per minute, or a heart rate that is above about 120 beats per minute.

74. The method, wherein said physiological characteristic is blood oxygen saturation and the predetermined amount is 5% below the baseline level, or is a difference of less than about 90% the absolute value of the baseline level.

75. The method, wherein said custodial care setting is a hospital, psychiatric institution, jail, prison, juvenile detention center, assisted living facility, group home, rehabilitation facility, or nursing home facility.

76. The method, wherein said monitoring device further comprises a tracking system.

77. The method, wherein said tracking system is capable of identifying where said at-risk individual is located within the custodial care setting.

78. The method, wherein said tracking system is capable of alerting said monitoring personnel as to the location of said at-risk individual within the custodial care setting.

79. The method, wherein said tracking system is capable of alerting said monitoring personnel when said at-risk individual enters a designated area.

80. The method, wherein said step of alerting comprises sounding an audible alarm.

81. The method, wherein said step of alerting comprises displaying a visual alarm.

82. The method, wherein said monitoring personnel is equipped with a remote device, and wherein said step of alerting comprises sending an alert to said remote device.

83. The method, wherein said alert comprises an alarm selected from the group consisting of audible alarms, visual alarms, vibrational alarms, and combinations thereof.

84. The method, further comprising a plurality of monitoring personnel, wherein each of said monitoring personnel is equipped with a remote device.

85. The method, wherein said monitoring device includes a storage means, and said monitoring device stores data identifying said at-risk individual.

86. The method, wherein said monitoring personnel is capable of preventing death by suicide attempt.

87. The method, wherein said suicide attempt is hanging.

88. The method, wherein said suicide attempt is asphyxiation.

89. The method, wherein said suicide attempt is severing a blood vessel.

90. A method if monitoring the health status of an at-risk individual, wherein said at-risk individual is maintained in a custodial care setting, comprising the steps of:
   (a) securing a monitoring device to said at-risk individual, wherein said monitoring device is capable of monitoring at least one physiological characteristic selected from the group consisting of pulse amplitude, heart rate and blood oxygen saturation of said at-risk individual;
   (b) setting forth a baseline level for said at-risk individual for said at least one physiological characteristic, wherein said baseline level is the level of said at least one physiological characteristic in a normal state;
   (c) continuously monitoring said at-risk individual for changes in said at least one physiological characteristic;
   (d) alerting at least one monitoring personnel when said at least one physiological characteristic is above said baseline level by a predetermined amount; and
   (e) said monitoring personnel responding by checking the status of said at-risk individual.

91. The method, wherein said physiological characteristic is the heart rate of said at-risk individual.

92. The method, wherein said predetermined amount is one of a difference of about 15-20 beats per minute between said monitored level and said baseline level, is below 50 beats per minute, or is above 120 beats per minute.

93. The method, wherein said physiological characteristic is blood oxygen saturation and the predetermined amount is 5% below the baseline level, or is a difference of less than about 90% the absolute value of the baseline level.

94. The method, wherein said health status comprises at least one heart malfunction.

95. The method, wherein said heart malfunction comprises a heart attack.

96. The method, wherein said heart attack stems from a panic attack suffered by said at-risk individual.

97. The method, wherein said heart attack stems from said at-risk individual taking a narcotic substance.

98. A device for detecting suicide attempts, comprising:
a monitoring device comprising a sensor capable of detecting at least one physiological state,
a transmitter,
a power source connected to the sensor and the transmitter;
wherein the sensor is adapted for attachment to a person above the neck.

99. The device, wherein the monitoring device further comprises a tracking device.

100. The device, wherein the monitoring device further comprises an inertial sensor.

101. The device, wherein the monitoring device is adapted for attachment to an ear.

102. The device, wherein the sensor is adapted for attachment to or insertion into an ear.

103. The device, wherein the sensor is adapted for attachment to the skin.

A computer program product comprising a computer readable storage medium having computer readable program code embodied therewith, the computer readable program code configured to perform operations, the operations comprising:
analyzing sensor data collected by a monitoring device secured to an at-risk individual, the data comprising at least one physiological characteristic of said at-risk individual;
determining if a first criterion for initiating an alert has been met for said at least one physiological characteristic and, if so,
initiating an alert to an alert device that said first criterion has been met for said at least one physiological characteristic.

What is claimed is:

1. A method of detecting an at-risk individual's attempt to commit suicide by means of reducing or completely obstructing the flow of blood to his or her brain and preventing said attempt to commit suicide from resulting in brain death or brain damage, wherein the at-risk individual maintained in a custodial care setting by at least one monitoring personnel, comprising the steps of:
    securing a monitoring device above the neckline of said at-risk individual, said monitoring device adapted with a sensor adapted to collect data on at least one physiological characteristic of blood flow above the neckline of said at-risk individual, wherein the data collected by the sensor on said at least one physiological characteristic of blood flow above the neckline reflects the blood supply to the brain of said at-risk individual;
    for each physiological characteristic, establishing a first criterion for initiating an alert, wherein said first criterion for initiating an alert indicates that blood flow above the neckline of said at-risk individual is completely blocked or is reduced to a level that may result in brain damage or brain death;
    monitoring said at least one physiological characteristic of said at-risk individual;
    analyzing the sensor data collected by said monitoring device on each at least one physiological characteristic to determine if said first criterion for initiating an alert has been met for said at least one physiological characteristic and, if so,
    initiating an alert to said at least one monitoring personnel that said first criterion has been met for said at least one physiological characteristic.

2. The method of claim 1, wherein said at least one physiological characteristic of blood flow above the neckline is selected from a group comprising pulse amplitude, blood pressure, pulse rate, presence or absence of a pulse, reduction of blood flow, level of blood flow, obstruction of blood flow, and tissue perfusion.

3. The method of claim 1, further comprising the step of said monitoring personnel responding by checking the status of said at-risk individual.

4. The method of claim 1, wherein the step of establishing a first criterion comprises the steps of:
    setting forth a baseline level for said at-risk individual for said at least one physiological characteristic, wherein said baseline level is the level of said at least one physiological characteristic in a normal state; and
    setting a pre-determined amount by which if said at least one physiological characteristic differs from said baseline level, an alert will be initiated.

5. The method of claim 2, wherein said monitoring device is secured to said at-risk individual at a suitable location above the neckline selected from a group comprising the ear, earlobe, ear concha, ear auricle, auditory canal, forehead, temple, jaw, chin, cheek, scalp, post-auricular area (behind ear), occipital area (back of neck/head), nose, nostrils, and a surface structure of the head.

6. The method of claim 5, wherein said monitoring device is secured to the ear of said at-risk individual by one of: attachment behind the ear of said at-risk individual; inserted at least partially into the ear canal of said at-risk individual; clipped to the ear lobe; and secured in the concha of the ear.

7. The method of claim 1, wherein said monitoring device is attached to headwear.

8. The method of claim 1, wherein at least two physiological characteristics are monitored.

9. The method of claim 1, wherein a first of said at least two physiological characteristics is blood flow above the neckline of said at-risk individual and a second of said at least two physiological characteristics is blood oxygen saturation.

10. The method of claim 1, wherein the step of establishing a first criterion further comprises establishing a second criterion for at least one of said at least one physiological characteristics that, if met, will cause an alert to be initiated.

11. The method of claim 1, wherein said custodial care setting is a hospital, psychiatric institution, jail, prison, juvenile detention center, assisted living facility, group home, rehabilitation facility, or nursing home facility.

12. The method of claim 1, wherein the step of analyzing the data collected by said monitoring device further comprises the step of determining the location of said monitoring device.

13. The method of claim 12, wherein the step of alerting at least one monitoring personnel includes communicating to said at least one monitoring personnel the location of said monitoring device.

14. The method of claim 12, wherein the step of determining the location of said monitoring device comprises analyzing a signal transmitted by the monitoring device or analyzing signals received by the monitoring device.

15. The method of claim 1, wherein the monitoring device is further adapted with a sensor capable of detecting whether the monitoring device has been removed by the at-risk individual.

16. The method of claim 1, wherein said first criterion for at least one of said at least one physiological characteristic is reduced or blocked blood flow above the neckline.

17. The method of claim 1, wherein the step of securing a monitoring device to said at-risk individual further comprises the step of providing an alert device to at least one monitoring personnel; and wherein the step of alerting at least one monitoring personnel comprises sending an alert to said alert device.

18. The method of claim 17, wherein said alert comprises an alarm selected from the group consisting of audible alarms, visual alarms, vibrational alarms, and combinations thereof.

19. The method of claim 1, wherein said monitoring device further includes a computer-readable medium, and said monitoring device stores data specific to said at-risk individual on said computer-readable medium.

20. A system for preventing a suicide attempt by an at-risk individual from resulting in brain death or brain damage to the at-risk individual, comprising:
a monitoring device adapted to be worn above the neck of the at-risk individual, the monitoring device comprising a sensor adapted to collect data on at least one physiological characteristic of blood flow above the neckline of said at-risk individual; and a first transmitter in communication with the sensor, the first transmitter adapted to send data relating to said at least one physiological characteristic;
a base station comprising a first receiver and a second transmitter; said first receiver adapted to receive said physiological characteristic data from said monitoring device, said second transmitter adapted to transmit an alert message;
an alert device comprising a second receiver to receive the alert message, and a signal generator adapted to generate an alert in the form of an audible, visual or tactile alarm;
a computer-readable medium, and
a processor coupled to said computer-readable medium, the processor adapted to execute program instructions to analyze data from the sensor of said at least one monitoring device, determine if blood flow above the neckline of said at-risk individual is reduced to a level that may result in brain damage or brain death or is completely blocked and, if so, initiate an alert to said alert device.

21. The system of claim 20, wherein said at least one physiological characteristic of blood flow above the neckline is selected from the group consisting of pulse amplitude, pulse rate, presence or absence of a pulse, reduction of blood flow, obstruction of blood flow, and tissue perfusion.

22. The system of claim 20, wherein said monitoring device is adapted to be secured to the at-risk individual at a suitable location above the neckline selected from a group comprising the ear, ear auricle, behind the ear (post-auricular area), ear canal, ear lobe concha of the ear, the auditory canal, forehead, temple, jaw, chin, cheek, scalp, occipital area (back of neck/head), nose, nostrils, and a surface structure of the head.

23. The system of claim 20, wherein said monitoring device is attached to headwear.

24. The system of claim 20, further comprising a remote monitoring station connected to the base station.

25. The system of claim 20, wherein said program instruction enables the processor to determine the location of each of the at least one monitoring devices.

26. The system of claim 20, where the at least one monitoring device incorporates a global positioning system receiver.

27. The system of claim 25, wherein the base station further comprises a display monitor, and the program instructions executing on the processor display the current status and location of each at least monitoring device.

28. The system of claim 20, wherein said base station is connected to a facility computer network, and any computer connected to said facility computer network is capable of operating as a remote monitoring station.

29. The system of claim 20, wherein said alert device is integrated with said base station.

30. The system of claim 29, further comprising one or more devices for receiving and retransmitting signal from the at least one monitoring device to the at least one alert devices.

31. The system of claim 20, wherein said at-risk individual is maintained in a custodial care setting.

32. The system of claim 20, further comprising a sensor adapted to detect the removal of the monitoring device from the at-risk individual; and wherein the processor also analyzes the data from said sensor adapted to detect removal of the monitoring device to determine whether the monitoring device has been removed from the at-risk individual and, if so, initiate an alert to said alert device.

* * * * *